(12) United States Patent
Fisher et al.

(10) Patent No.: US 12,050,194 B2
(45) Date of Patent: Jul. 30, 2024

(54) SENSING SYSTEMS

(71) Applicant: ILLUMINA, INC., San Diego, CA (US)

(72) Inventors: Jeffrey S. Fisher, San Diego, CA (US); Brian D. Mather, San Diego, CA (US); Kaitlin M. Pugliese, San Diego, CA (US); Jeffrey G. Mandell, La Jolla, CA (US); Maria Candelaria Rogert Bacigalupo, Encinitas, CA (US); Boyan Boyanov, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 801 days.

(21) Appl. No.: 17/257,464

(22) PCT Filed: Jan. 24, 2020

(86) PCT No.: PCT/US2020/014942
§ 371 (c)(1),
(2) Date: Dec. 31, 2020

(87) PCT Pub. No.: WO2020/167447
PCT Pub. Date: Aug. 20, 2020

(65) Prior Publication Data
US 2021/0310985 A1 Oct. 7, 2021

Related U.S. Application Data

(60) Provisional application No. 62/806,545, filed on Feb. 15, 2019.

(51) Int. Cl.
*G01N 27/414* (2006.01)
*C12Q 1/00* (2006.01)
(Continued)

(52) U.S. Cl.
CPC ........ *G01N 27/4145* (2013.01); *C12Q 1/001* (2013.01); *C12Q 1/48* (2013.01); *C12Q 1/6825* (2013.01)

(58) Field of Classification Search
None
See application file for complete search history.

(56) References Cited

U.S. PATENT DOCUMENTS 7,198,776 B2 4/2007 Klaveness et al.
7,686,929 B2 3/2010 Toumazou et al.
(Continued)

FOREIGN PATENT DOCUMENTS

CN 105378113 A 3/2016
CN 107075579 A 8/2017
(Continued)

OTHER PUBLICATIONS

"Ion semiconductor sequencing" Wikipedia, 2018, 5 pages https://en.wikipedia.org/w/index.php?title=Ion_semiconductor_sequencing&oldid=863915756.
(Continued)

*Primary Examiner* — J. Christopher Ball
(74) *Attorney, Agent, or Firm* — Dierker & Kavanaugh, P.C.

(57) ABSTRACT

In an example, a sensing system includes a pH sensor. The pH sensor includes two electrodes and a conductive channel operatively connected to the two electrodes. A complex is attached to the conductive channel of the pH sensor. The complex includes a polymerase linked to at least one pH altering moiety that is to participate in generating a pH change within proximity of the conductive channel from consumption of a secondary substrate in a fluid that is exposed to the pH sensor. The at least one pH altering
(Continued)

moiety is selected from the group consisting of an enzyme, a metal coordination complex, a co-factor, and an activator.

18 Claims, 4 Drawing Sheets

(51) Int. Cl.
  *C12Q 1/48* (2006.01)
  *C12Q 1/6825* (2018.01)

(56) References Cited

U.S. PATENT DOCUMENTS

| | | |
|---|---|---|
| 8,492,799 B2 | 7/2013 | Rothberg et al. |
| 9,944,969 B2 | 4/2018 | Knopfmacher et al. |
| 2006/0194263 A1 | 8/2006 | Boussaad et al. |
| 2009/0134042 A1 | 5/2009 | Nomoto et al. |
| 2009/0286245 A1 | 11/2009 | Bjornson et al. |
| 2013/0189699 A1 | 7/2013 | Ou et al. |
| 2014/0357515 A1 | 12/2014 | Friedrich et al. |
| 2015/0111759 A1 | 4/2015 | Ju et al. |
| 2016/0068902 A1 | 3/2016 | Farinas |
| 2017/0038333 A1* | 2/2017 | Turner ................ C12Q 1/6874 |

FOREIGN PATENT DOCUMENTS

| | | |
|---|---|---|
| GB | 2509481 | 7/2014 |
| RU | 2644263 C2 | 2/2018 |
| WO | WO 2010/037085 | 4/2010 |
| WO | 2014110287 A1 | 7/2014 |
| WO | 2016010975 A2 | 1/2016 |
| WO | 2017203059 A1 | 11/2017 |

OTHER PUBLICATIONS

Chen, C.Y. "DNA polymerases drive DNA sequencing-by-synthesis technologies: both past and present", Frontiers in Microbiology, vol. 5, Article 305, 2014, pp. 1-11.

Welter, M. et al., "Sequence-Specific Incorporation of Enzyme-Nucleotide Chimera by DNA Polymerases" Angewandte Chemie International Edition, 55(34), 2016, pp. 10131-10135.

Kwon, S. J. et al., "An electrochemical immunosensor using p-aminophenol redox cycling by NADH on a self-assembled monolayer and ferrocene-modified Au electrodes", The Royal Society of Chemistry 2008, Analyst, 133(11), pp. 1599-1604.

Shin, K., et al. "Novel T-Channel Nanowire FET With Built-in Signal Amplification for pH Sensing", 2009 IEEE International Electron Devices Meeting (IEDM), Corpus ID: 32264188, 2009, 4 pages.

* cited by examiner

SENSING SYSTEMS

CROSS-REFERENCE TO RELATED APPLICATION

This application is a national stage entry under 35 U.S.C. § 371 of PCT/US2020/014942, filed Jan. 24, 2020, which itself claims the benefit of U.S. Provisional Application Ser. No. 62/806,545, filed Feb. 15, 2019; the content of each of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions generate fluorescence, and thus an optical system may be used for detection. In other examples, the controlled reactions alter charge, conductivity, or some other electrical property, and thus an electronic system may be used for detection.

INTRODUCTION

A first aspect disclosed herein is a sensing system comprising a pH sensor, including two electrodes and a conductive channel operatively connected to the two electrodes; and a complex attached to the conductive channel of the pH sensor, the complex including a polymerase linked to at least one pH altering moiety that is to participate in generating a pH change within proximity of the conductive channel from consumption of a secondary substrate in a fluid that is exposed to the pH sensor, the at least one pH altering moiety being selected from the group consisting of an enzyme, a metal coordination complex, a co-factor, and an activator.

In an example of this first aspect, the at least one pH altering moiety is the enzyme, and wherein the enzyme generates an acid or a base in a reaction with the secondary substrate. In one specific example, the enzyme is selected from the group consisting of hydrolases and oxidases.

In an example of this first aspect, kinetics of the at least one pH altering moiety are at least 10 fold faster than kinetics of the polymerase.

In an example of this first aspect, the at least one pH altering moiety is the enzyme, and the complex further comprises a nucleic acid hairpin-enzyme inhibitor conjugate attached to the enzyme.

In an example of this first aspect, the at least one pH altering moiety is the enzyme; and the complex further includes a second enzyme attached to the polymerase.

In an example of this first aspect, the complex is a fusion protein or a protein chimera.

In an example of this first aspect, the conductive channel of the pH sensor is selected from the group consisting of a semi-conducting nanostructure, a graphene nanostructure, a metallic nanostructure, and a conducting polymer nanostructure.

An example of this first aspect further comprises a support including a plurality of depressions separated by interstitial regions, wherein at least the conductive channel of the pH sensor is at a bottom of one of the plurality of depressions; and a plurality of additional pH sensors, wherein at least a conductive channel of each of the plurality of additional pH sensors is at a bottom of a respective one of the plurality of depressions. In one specific example, each of the plurality of depressions includes sidewalls, and wherein the sidewalls include a pH buffer material.

It is to be understood that any features of the sensing system disclosed herein may be combined together in any desirable manner and/or configuration.

A second aspect disclosed herein is a kit comprising a pH sensor, including two electrodes and a conductive channel operatively connected to the two electrodes; and a fluid, including a liquid carrier and a complex in the liquid carrier, the complex including a polymerase linked to at least one enzyme that is to create a pH change within proximity of the conductive channel from consumption of a secondary substrate in a second fluid that is exposed to the pH sensor.

An example of this second aspect further comprises the second fluid including a second liquid carrier and a labeled nucleotide, which includes a nucleotide, a linking molecule attached to a terminal phosphate group of the nucleotide, and a label attached to the linking molecule, the label being selected from the group consisting of a first group that enhances kinetics of the enzyme and a second group that slows kinetics of the enzyme. In one specific example, the secondary substrate is in the second fluid and is a separate molecule from the labeled nucleotide, and the first group or the second group is to alter kinetics of an acid or base generating reaction involving the enzyme and the secondary substrate. In another specific example, the secondary substrate is in the second fluid and is a separate molecule from the labeled nucleotide, the label is the second group that slows kinetics of the enzyme, and the second group is selected from the group consisting of an allosteric inhibitor, a steric exclusion group, and a buffering group. In still another specific example, the secondary substrate is in the second fluid and is a separate molecule from the labeled nucleotide, the label is the first group that that enhances kinetics of the enzyme, and the first group is a co-factor of the enzyme.

Another example of this second aspect further comprises the second fluid including a second liquid carrier and a labeled nucleotide, which includes a nucleotide and the secondary substrate attached to a base or a sugar of the nucleotide, wherein kinetics of the secondary substrate are at least 10 fold faster than kinetics of the polymerase.

It is to be understood that any features of the kit may be combined together in any desirable manner. Moreover, it is to be understood that any combination of features of this kit and/or of the sensing system may be used together, and/or combined with any of the examples disclosed herein.

A third aspect disclosed herein is a kit comprising a pH sensor including two electrodes and a conductive channel operatively connected to the two electrodes, and a fluid including a liquid carrier and a complex in the liquid carrier, the complex including a polymerase linked to a metal coordination complex that is to create a pH change within proximity of the conductive channel from consumption of a secondary substrate in a second fluid that is exposed to the pH sensor.

An example of this third aspect further comprises the second fluid including a second liquid carrier; the secondary substrate (wherein the secondary substrate is to generate an acid or base through a reaction with the metal coordination complex), and a labeled nucleotide, which includes a nucleotide, a linking molecule attached to a terminal phosphate group of the nucleotide, and a label attached to the linking molecule, the label being a ligand for a metal of the metal coordination complex, wherein the ligand alters a catalytic property of the metal coordination complex.

It is to be understood that any features of this kit may be combined together in any desirable manner. Moreover, it is to be understood that any combination of features of this kit and or of the sensing system and/or of the other kit may be used together, and/or combined with any of the examples disclosed herein.

A fourth aspect disclosed herein is a labeled nucleotide comprising a nucleotide, a linking molecule attached to a terminal phosphate group of the nucleotide, and a catalyst label attached to the linking molecule, wherein the catalyst label is to create a pH change from consumption of a secondary substrate in a fluid with the labeled nucleotide.

In an example of the fourth aspect, the catalyst label is selected from the group consisting of hydrolases and oxidases.

It is to be understood that any features of this labeled nucleotide may be combined together in any desirable manner. Moreover, it is to be understood that any combination of features of this labeled nucleotide and/or of the sensing system and/or of the kits may be used together, and/or combined with any of the examples disclosed herein.

A fifth aspect disclosed herein is a kit comprising the labeled nucleotide of the fourth aspect, and a sensing system, including two electrodes, a conductive channel operatively connected to the two electrodes, and a complex attached to the conductive channel, the complex including a polymerase conjugated to a co-factor or an activator of the catalyst label of the labeled nucleotide.

It is to be understood that any features of this kit may be combined together in any desirable manner. Moreover, it is to be understood that any combination of features of this kit and/or of the sensing system and/or of the other kits and/or of the labeled nucleotide may be used together, and/or combined with any of the examples disclosed herein.

A sixth aspect disclosed herein is a labeled nucleotide comprising a nucleotide having a 3' OH blocking group, a cleavable linking molecule attached to a base or a sugar of the nucleotide, and a label attached to the cleavable linking molecule, wherein the label is to participate in a pH altering reaction involving the secondary substrate.

It is to be understood that any features of this labeled nucleotide may be combined together in any desirable manner. Moreover, it is to be understood that any combination of features of this labeled nucleotide and/or of the sensing system and/or of the kits and/or of the other labeled nucleotide may be used together, and/or combined with any of the examples disclosed herein.

A seventh aspect disclosed herein is a kit comprising the labeled nucleotide of the sixth aspect, and a sensing system, including two electrodes, a conductive channel operatively connected to the two electrodes, and a complex attached to the conductive channel, the complex including a polymerase conjugated to a co-factor or an activator of the catalyst label of the labeled nucleotide.

It is to be understood that any features of this kit may be combined together in any desirable manner. Moreover, it is to be understood that any combination of features of this kit and/or of the sensing system and/or of the kits and/or of the labeled nucleotides may be used together, and/or combined with any of the examples disclosed herein.

An eighth aspect disclosed herein is a method comprising introducing a fluid to a sensor array including a plurality of individually addressable conductive channels, thereby attaching a complex to at least some of the plurality of individually addressable conductive channels, the complex including a polymerase and a pH altering moiety linked to the polymerase, the pH altering moiety being selected from the group consisting of an enzyme that is to catalyze consumption of a secondary substrate in a solution that is to be exposed to the sensor array, a metal coordination complex that is to catalyze consumption of the secondary substrate in the solution that is to be exposed to the sensor array, and a co-factor or activator of a catalyst label attached to a labeled nucleotide that is to be introduced to the sensor array.

It is to be understood that any features of this method may be combined together in any desirable manner. Moreover, it is to be understood that any combination of features of this method and/or of the sensing system and/or of the kits and/or of the labeled nucleotides may be used together, and/or combined with any of the examples disclosed herein.

A ninth aspect disclosed herein is a method comprising introducing a template polynucleotide chain to a sensor having a polymerase tethered to a conductive channel; introducing a fluid including a secondary substrate and labeled nucleotides to the sensor, whereby a nucleotide of one of the labeled nucleotides associates with the polymerase and a label of the one of the labeled nucleotides participates in a pH altering reaction involving the secondary substrate that is within proximity of the conductive channel; and detecting a response of the conductive channel.

In an example of this ninth aspect, the polymerase of the sensor is part of a complex with an enzyme catalyst, the label is a group that enhances or slows kinetics of the enzyme catalyst, and the method further comprises detecting a change in charge compared to a baseline charge.

In an example of this ninth aspect, the polymerase of the sensor is part of a complex with an enzyme catalyst, the label is the secondary substrate, and the method further comprises detecting a change in charge compared to a baseline charge.

In an example of this ninth aspect, the polymerase of the sensor is part of a complex with a metal coordination complex, the label is a ligand for a metal of the metal coordination complex, and the method further comprises detecting a change in charge compared to a baseline charge.

In an example of this ninth aspect, the polymerase of the sensor is part of a complex with an enzyme catalyst, a nucleic acid hairpin-enzyme inhibitor conjugate is attached to the enzyme catalyst, the label is an oligonucleotide sequence that is complementary to a portion of the nucleic acid hairpin-enzyme inhibitor conjugate, and the method further comprises detecting a change in charge compared to a baseline charge.

Any one or more of the examples of the ninth aspect may further comprise identifying the nucleotide associated with the polymerase from the change in charge or a rate of the change in charge.

In an example of this ninth aspect, the labeled nucleotides have distinct incorporation rates, and the method further comprises identifying the associated labeled nucleotide by its distinct incorporation rate.

It is to be understood that any features of this method may be combined together in any desirable manner. Moreover, it is to be understood that any combination of features of this method and/or of the other methods and/or of the sensing system and/or of the kits and/or of the labeled nucleotides may be used together, and/or combined with any of the examples disclosed herein.

A tenth aspect disclosed herein is a method comprising selecting a pH altering moiety from the group consisting of an enzyme that is to catalyze consumption of a secondary substrate in a solution, a metal coordination complex that is to catalyze consumption of the secondary substrate in the solution, and a co-factor or activator of a catalyst label attached to a labeled nucleotide; conjugating a polymerase to the pH altering moiety to generate a complex; and attaching the complex to a conductive channel operatively connected to two electrodes.

It is to be understood that any features of this method may be combined together in any desirable manner. Moreover, it is to be understood that any combination of features of this method and/or of the other methods and/or of the sensing system and/or of the kits and/or of the labeled nucleotides may be used together, and/or combined with any of the examples disclosed herein.

An eleventh aspect disclosed herein is an incorporation mix, comprising a liquid carrier; a complex including a polymerase and a pH altering moiety linked to the polymerase, the pH altering moiety being selected from the group consisting of an enzyme that is to catalyze consumption of a secondary substrate, a metal coordination complex that is to catalyze consumption of the secondary substrate, and a co-factor or activator that is to catalyze consumption of the secondary substrate; and a labeled nucleotide, including a nucleotide, a linking molecule attached to a terminal phosphate group of the nucleotide, and a label attached to the linking molecule, wherein the label is to participate in a pH altering reaction involving the secondary substrate.

In an example of this eleventh aspect, the pH altering moiety is the enzyme, and the label is selected from the group consisting of a first group that enhances kinetics of the enzyme and a second group that slows kinetics of the enzyme; the pH altering moiety is the metal coordination complex, and the label is a ligand for a metal of the metal coordination complex, wherein the ligand alters a catalytic property of the metal coordination complex; or the pH altering moiety is the co-factor or activator, and the label is a catalyst label that is activated by the co-factor or activator.

In an example of this eleventh aspect, the pH altering moiety is the enzyme; the complex further includes a nucleic acid hairpin-enzyme inhibitor conjugate attached to the enzyme; and the label is an oligonucleotide sequence that is complementary to a portion of the nucleic acid hairpin-enzyme inhibitor conjugate.

It is to be understood that any features of this incorporation mix may be combined together in any desirable manner. Moreover, it is to be understood that any combination of features of the incorporation mix and/or of the methods and/or of the sensing system and/or of the kits and/or of the labeled nucleotides may be used together, and/or combined with any of the examples disclosed herein.

A twelfth aspect disclosed herein is a kit comprising the incorporation mix of the eleventh aspect, and a secondary substrate mix including a second liquid carrier and the secondary substrate.

An example of the twelfth aspect further comprises a flow cell, including a substrate including a plurality of depressions separated by interstitial regions; a conductive channel at a bottom of each of the plurality of depressions; and at least one primer grafted in each in each of the depressions.

It is to be understood that any features of this kit may be combined together in any desirable manner. Moreover, it is to be understood that any combination of features of this kit and/or of the incorporation mix and/or of the methods and/or of the sensing system and/or of the other kits and/or of the labeled nucleotides may be used together, and/or combined with any of the examples disclosed herein.

A thirteenth aspect disclosed herein is an incorporation mix comprising a liquid carrier including a buffer; a complex including a polymerase and a pH altering moiety linked to the polymerase, the pH altering moiety being selected from the group consisting of an enzyme that is to catalyze consumption of a secondary substrate, a metal coordination complex that is to catalyze consumption of the secondary substrate, and a co-factor or activator that is to catalyze consumption of the secondary substrate; and a labeled nucleotide, including a nucleotide having a 3' OH blocking group, a cleavable linking molecule attached to a base or a sugar of the nucleotide, and a label attached to the linking molecule, wherein the label is to participate in a pH altering reaction involving the secondary substrate.

In an example of the thirteenth aspect, the pH altering moiety is the enzyme, and the label is selected from the group consisting of a first group that enhances kinetics of the enzyme, a second group that slows kinetics of the enzyme, and the secondary substrate; or the pH altering moiety is the metal coordination complex, and the label is a ligand for a metal of the metal coordination complex, wherein the ligand alters a catalytic property of the metal coordination complex; or the pH altering moiety is the co-factor or activator, and the label is a catalyst label that is activated by the co-factor or activator.

In an example of the thirteenth aspect, the pH altering moiety is the enzyme; the complex further includes a nucleic acid hairpin-enzyme inhibitor conjugate attached to the enzyme; and the label is an oligonucleotide sequence that is complementary to a portion of the nucleic acid hairpin-enzyme inhibitor conjugate.

It is to be understood that any features of this incorporation kit may be combined together in any desirable manner. Moreover, it is to be understood that any combination of features of this incorporation mix and/or of the methods and/or of the sensing system and/or of the kits and/or of the labeled nucleotides may be used together, and/or combined with any of the examples disclosed herein.

A fourteenth aspect disclosed herein is a kit comprising the incorporation mix as defined in the thirteenth aspect, and a secondary substrate mix including a second liquid carrier and the secondary substrate.

An example of the fourteenth aspect further comprises a flow cell, including a substrate including a plurality of depressions separated by interstitial regions; a conductive channel at a bottom of each of the plurality of depressions; and a primer grafted in each of the depressions.

An example of the fourteenth aspect further comprises a de-blocking agent solution.

It is to be understood that any features of this kit may be combined together in any desirable manner. Moreover, it is to be understood that any combination of features of this kit and/or of the methods and/or of the sensing system and/or of the other kits and/or of the labeled nucleotides and/or of the incorporation mix may be used together, and/or combined with any of the examples disclosed herein.

Still further, it is to be understood that any features of any of the aspects may be used alone or in combination in any desirable manner, and/or may be combined with any of the examples disclosed herein at least to achieve the benefits as described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 7A is a top view of an example of a flow cell;

DETAILED DESCRIPTION

Figure 1:
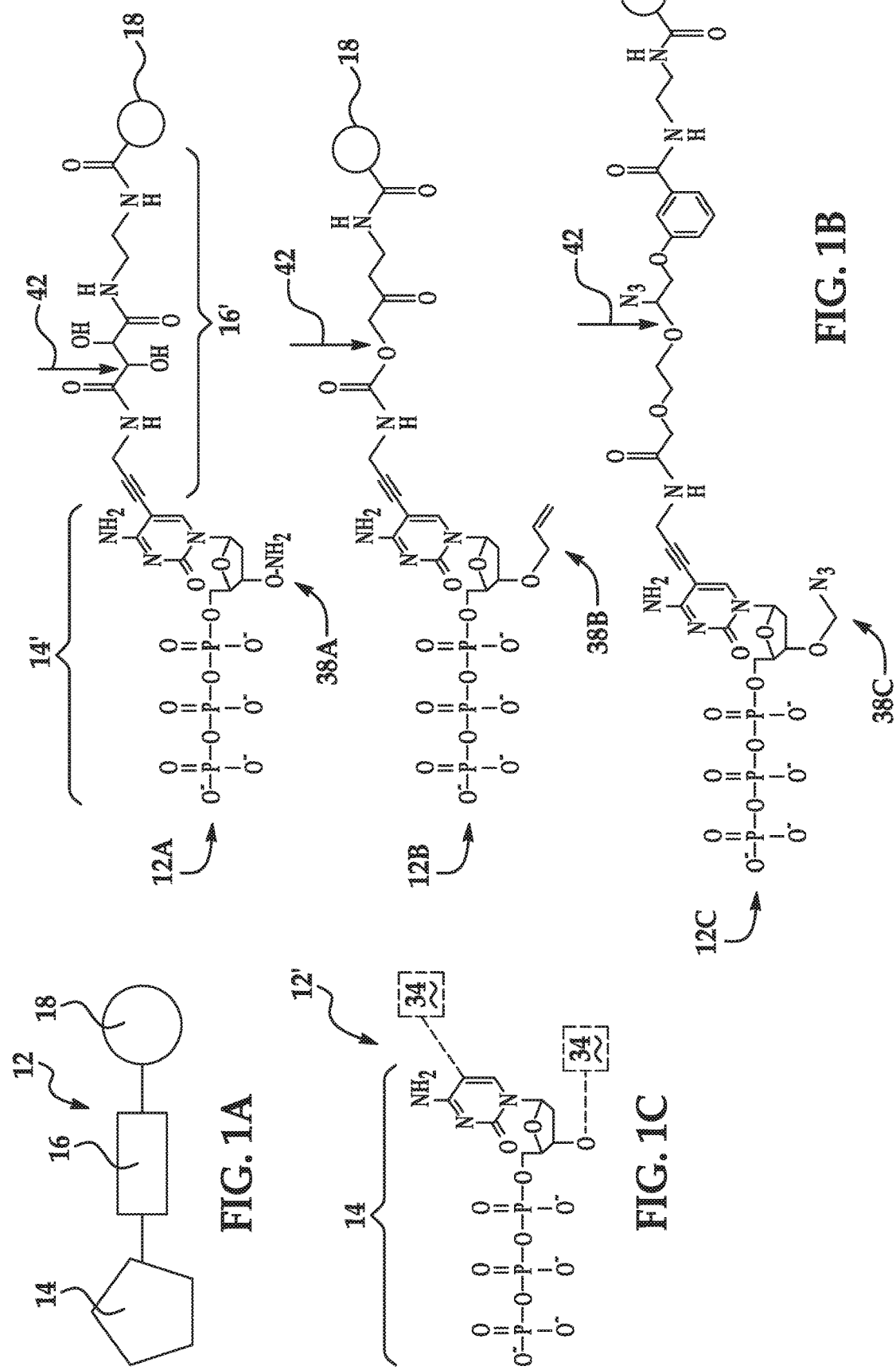
FIGS. 1A through 1C are schematic illustrations of different examples of labeled nucleotides disclosed herein.

Some of the example sensing systems disclosed herein may be used for single molecule detection in nucleic acid sequencing procedures. Each of these sensing systems includes one conductive channel with one polymerase or one polymerase-containing complex attached thereto. This conductive channel can detect a change in charge as a result of a localized change in pH (hydrogen ion concentration). In use, labeled nucleotides and a secondary substrate are introduced to the sensing system. As a nitrogenous base of one of the labeled nucleotides is incorporated into a nascent strand by the polymerase, the secondary substrate is consumed in an acid or base generating reaction (which increases or decreases the concentration of charged ions). The acid or base generating reaction also involves a pH altering moiety, which, in some examples, is immobilized on the conductive channel as part of a complex; and, in other examples, is a label of the incorporated labeled nucleotide. Some of the acid or base generating reactions involve multiple pH altering moieties, e.g., one as part of the complex and another as a label of the labeled nucleotide. These configurations enable the pH altering moiety to be located at or near the surface of the conductive channel; and thus, the acid or base generating reaction is localized at the surface of the conductive channel. In some instances, the charged ions react with surface groups of the conductive channel, causing protonation or deprotonation of the surface groups, which alters the charge of the surface groups. In these instances, the charge of the surface groups is sensed. Because the charges are directly on the surface of the conductive channel, they cannot be efficiently screened by ions in solution and thus can induce large changes in threshold voltage and current. In other instances, the charged ions resulting from acid or base generation are sensed.

Some other of the example sensing systems disclosed herein may be used for ensemble nucleic acid sequencing procedures. Each of these sensing systems includes a conductive channel with a lawn of primers (e.g., oligo pairs) thereon. This conductive channel can detect a change in charge as a result of a localized change in pH. In use, library templates are introduced and hybridized to the primers. Cluster generation is performed to generate several template polynucleotide chains. Polymerase-containing complexes, labeled nucleotides, and secondary substrates are then introduced to the sensing system. During or after a nitrogenous base of respective labeled nucleotides are incorporated (by respective polymerases of the complexes) into respective nascent strands formed along the respective template polynucleotide chains, the secondary substrates are consumed in an acid or base generating reaction (which increases or decreases the concentration of charged ions). Similar to the single molecule sensing, the acid or base generating reaction also involves a pH altering moiety, which is part of the polymerase-containing complex or is a label of the incorporated labeled nucleotides. These configurations enable the pH altering moiety to be located at or near the surface of the conductive channel; and thus, the acid or base generating reaction is localized at the surface of the conductive channel. Either the charged ions or the reaction of the charged ions with surface groups of the conductive channel are sensed.

In any of the examples disclosed herein, the acid or base generating reactions can generate hundreds, or thousands, or even more protons or molecules of base, thereby generating a large and localized pH change.

In any of the examples disclosed herein, the pH altering moiety may be any chemical species that can participate in an acid or base generating reaction with the secondary substrate, or modify the activity of another pH altering moiety that is acting on the secondary substrate. As examples, the pH altering moiety may catalyze (cause or accelerate) the acid or base generating reaction involving the secondary substrate, may inhibit the acid or base generating reaction involving the secondary substrate, may enhance or slow down the acid or base generating reaction kinetics, or may otherwise participate in the acid or base generating reaction involving the secondary substrate. Some examples of the pH altering moiety are immobilized on the conductive channel as part of a complex; and other examples of the pH altering moiety are a label of the incorporated labeled nucleotide. In some cases, two pH altering moieties may interact together to produce a pH change.

The acid or base generating (pH altering) reactions disclosed herein involve the secondary substrate. As used herein, the term "secondary substrate" refers to a chemical species that is consumed in a reaction that generates an acid or a base, where the chemical species is a separate molecule from a nucleotide whose base is capable of interacting with a polymerase of the complex or is a distinct molecule attached to the sugar or the base of the nucleotide whose base is capable of interacting with a polymerase of the complex, and is not a by-product of the nitrogenous base incorporation event. The use of the distinct secondary substrate enables the kinetics of the detected pH change to be decoupled from the kinetics of the nucleotide incorporation. In some examples, the pH altering moiety that interacts with the secondary substrate may be significantly kinetically faster than the polymerase that interacts with the nucleotide. This enables a larger pH change to be observed for a single incorporation event or for a group of incorporation events.

It is desirable for the acid or base generating (pH altering) reactions to take place within proximity of the conductive channel. "Within proximity" generally refers to any distance over which the generated acid or base can diffuse. In an array with repeating/periodic sensing systems, "within proximity" may be defined in terms of the sensor/sensing system pitch. The sensor pitch or sensing system pitch refers to the distance between two successive sensors/sensing systems along a line. In an example, the reaction zone (where the acid or base is generated) of the sensing system may be within % of the sensor pitch from the conductive channel of the sensing system.

Several examples of the sensing system 10A-10E for single molecule sensing are disclosed herein, and are shown and described in FIG. 2, FIG. 3A, FIG. 3B, FIG. 4, FIG. 5, FIG. 6A and FIG. 6B. An example of the sensing systems 40A and 40B for ensemble sequencing are shown in FIG. 7C and FIG. 7D. Each example of the sensing system 10A-10E or 40A-40B may be used with a labeled nucleotide. Some labeled nucleotides are capable of naturally cleaving after base incorporation, and this example is schematically shown in FIG. 1A. Some other labeled nucleotides include a reversible terminator that allows only a single-base incorporation to occur in each sequencing cycle, and examples of the chemical structure of some of these labeled nucleotides are shown in FIG. 1B. Any of these examples may also include the secondary substrate as a distinct molecule attached to the sugar or base (FIG. 1C). Each of the labeled nucleotides will now be described.

Labeled Nucleotides

As depicted in FIG. 1A, the labeled nucleotide 12 includes a nucleotide 14, a linking molecule 16 attached to a terminal phosphate group of the nucleotide 14, and a label 18 attached to the linking molecule 16. The labeled nucleotide 12 may be considered a non-natural or synthetic nucleotide because it is structurally or chemically distinct from a natural nucleotide.

The nucleotide 14 of the labeled nucleotide 12 may be a natural nucleotide. Natural nucleotides include a nitrogen-containing heterocyclic base (or nitrogenous base), a sugar, and one or more phosphate groups. Examples of natural nucleotides include, for example, ribonucleotides or deoxyribonucleotides. In a ribonucleotide, the sugar is a ribose, and in a deoxyribonucleotide, the sugar is a deoxyribose (i.e., a sugar lacking a hydroxyl group that is present at the 2' position in ribose). In an example, the nucleotide 14 is in the polyphosphate form because it includes several phosphate groups (e.g., tri-phosphate (i.e., gamma phosphate), tetra-phosphate, penta-phosphate, hexa-phosphate, etc.). The heterocyclic base can be a purine base or a pyrimidine base or any other nucleobase analog. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The labeled nucleotide 12 also includes the linking molecule 16. The linking molecule 16 may be any long chain molecule that can chemically bond, at one end, to the phosphate group(s) of the nucleotide 14 and that can chemically bond, at the other end, to the label 18. In some instances, the linking molecule 16 may also be selected so that it does not interact with the polymerase 28 (see, e.g., FIG. 2, FIG. 3A, FIG. 4, FIG. 5, FIG. 6A, and FIG. 6B). In other instances, the linking molecule 16 may also be selected so that it weakly interacts with the polymerase 28, as this weak interaction can help to guide the label 18 within proximity of the conductive channel. The linking molecule 16 may be selected so that it is long enough to permit the label 18 to associate with a pH altering moiety and/or a secondary substrate 34 (see, e.g., FIG. 2) while, for example, the nucleotide 14 is held by the polymerase 28 during an incorporation event.

As examples, the linking molecule 16 may include an alkyl chain, a poly(ethylene glycol) chain, an amido group, a phosphate group, a heterocycle such as a triazole, nucleotides, or combinations thereof. Examples of the alkyl chain may include at least 6 carbon atoms and examples of the poly(ethylene glycol) chain may include at least 3 ethylene glycol units.

The following example illustrates an example of the labeled nucleotide 12, where the linking molecule 16 comprises an alkyl chain, an amide group, a poly(ethylene glycol) chain, and a triazole:

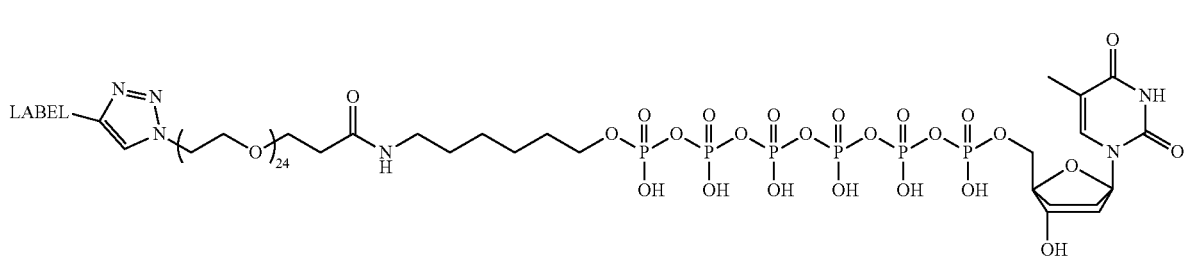

The following example illustrates another example of the labeled nucleotide 12, where the linking molecule 16 comprises alkyl chains, an amide group, poly(ethylene glycol) chains, a triazole, and a phosphate group:

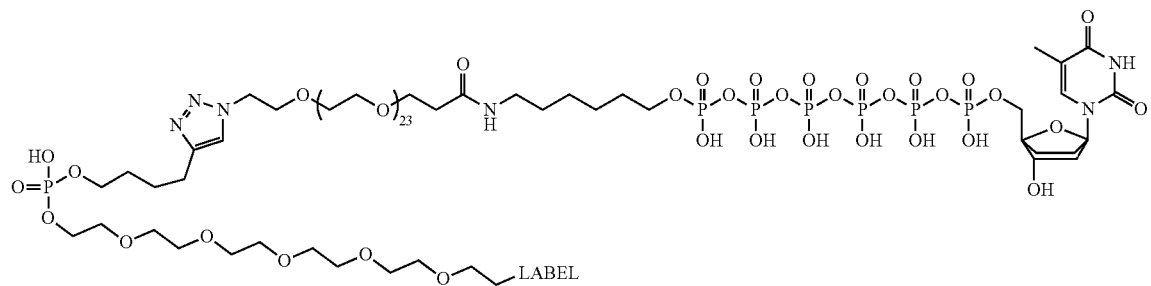

The following example illustrates yet another example of the labeled nucleotide 12, where the linking molecule 16 comprises alkyl chains, amide groups, poly(ethylene glycol) chains, a triazole, and a phosphate group:

While several example linking molecules 16 have been described, it is to be understood that other linking molecules 16 may be used. The selection of the linking molecule 16 will depend, in part, on the label 18 that is to be attached to

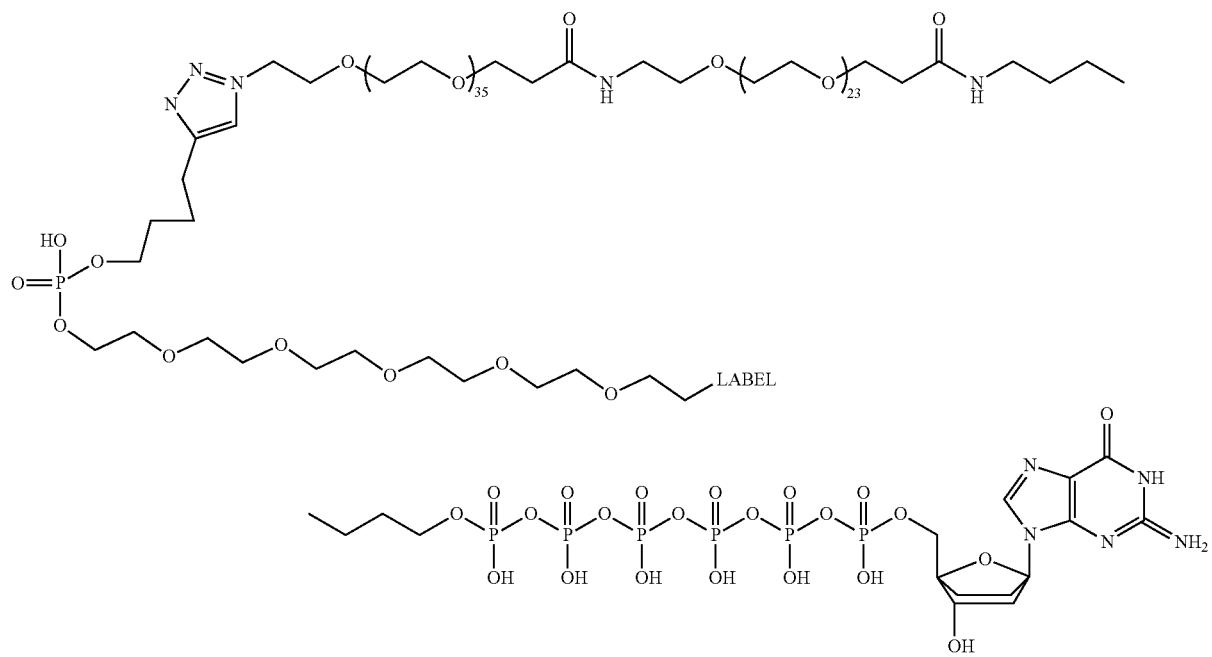

The following example illustrates still a further example of the labeled nucleotide 12, where the linking molecule 16 comprises alkyl chains, an amide group, poly(ethylene glycol) chains, a triazole, a phosphate group and a polynucleotide chain:

the nucleotide 14. Moreover, the length of the linking molecule 16 may be selected so that when a respective nucleotide 14 is held by a polymerase of an individual sensing system, the respective label 18 can participate in the

Figure 2:
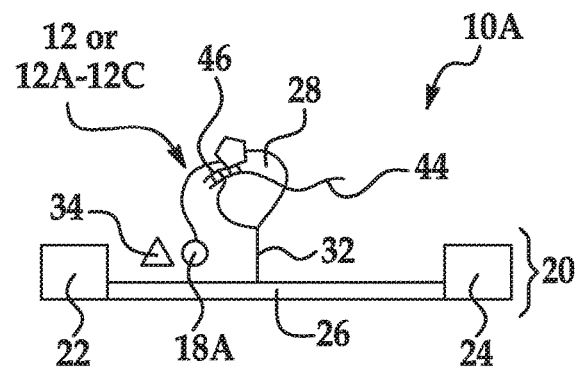
FIG. 2 is a schematic illustration depicting one example of the sensing system disclosed herein, and an example of a labeled nucleotide and a secondary substrate that may be used with this example of the sensing system.

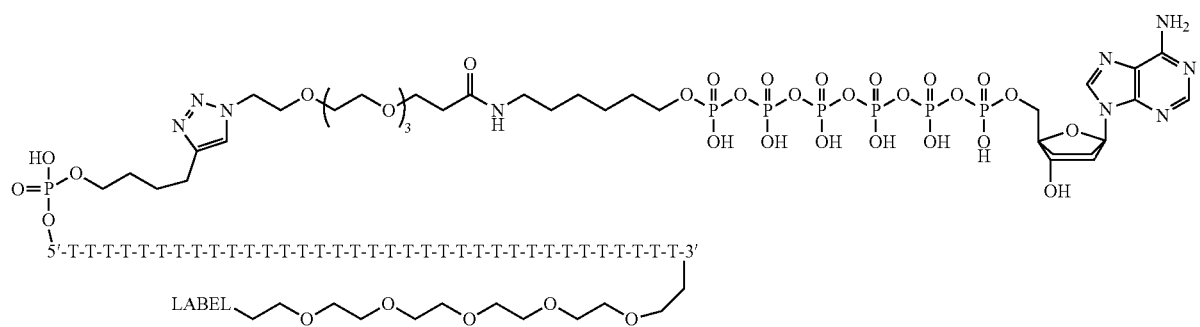

acid or base generating reaction at the surface of the conductive channel 26 (see, e.g., FIG. 2).

In each example labeled nucleotide 12, the label 18 is attached (through the linking molecule 16) to the terminal phosphate end of the nucleotide 14. Attachment at the terminal phosphate end may be desirable in some sequencing techniques because after nucleotide base incorporation, the bond between the alpha phosphate and the linking molecule 16 or between the alpha phosphate and beta phosphate is naturally cleaved. This natural cleavage enables the label 18 (and the linking molecule 16) to dissociate from the incorporated nucleotide base and diffuse away from the sensing system 10A-10E, so that another labeled nucleotide 12 can associate with the polymerase 28 of the sensing system 10A-10E and so that a previously incorporated base does not create lasting signals that interfere with the detection of the next incorporated base.

The label 18 that is included in the labeled nucleotide 12 may depend, in part, upon the sensing system 10A-10E or 40A-40B that is to be used with the labeled nucleotide 12. Different labels 18 will be described further in reference to each of the sensing systems 10A-10E and 40A-40B.

As depicted in FIG. 1B, each of the labeled nucleotide 12A, 12B, 12C includes a nucleotide 14' having a 3' OH blocking group 38A, 38B, 38C, a cleavable linking molecule 16' attached to a base or a sugar of the nucleotide 14', and a label 18 attached to the linking molecule 16'.

The nucleotide 14' may be any of the examples set forth for the nucleotide 14. In the examples disclosed herein, the nucleotide 14' has a 3' OH blocking group 38A, 38B, 38C attached thereto. The 3' OH blocking group 38A, 38B, 38C may be linked to an oxygen atom of the sugar molecule in the nucleotide 14'. The 3' OH blocking group 38A, 38B, 38C may be a reversible terminator that allows only a single-base incorporation to occur in each sequencing cycle. The reversible terminator stops additional bases from being incorporated into a nascent strand that is complementary to a template polynucleotide chain. This enables the detection and identification of a single incorporated base. The 3' OH blocking group 38A, 38B, 38C can subsequently be removed, enabling additional sequencing cycles to take place at each template polynucleotide chain. Examples of different 3' OH blocking groups 38A, 38B, 38C are shown in FIG. 1B, including a 3'-ONH$_2$ reversible terminator (shown at 38A), a 3'—O-allyl reversible terminator (—CH=CHCH$_2$, shown at 38B), and 3'-O-azidomethyl reversible terminator (—CH$_2$N$_3$, shown at 38C). Other suitable reversible terminators include o-nitrobenzyl ethers, alkyl o-nitrobenzyl carbonate, ester moieties, other allyl-moieties, acetals (e.g., tert-butoxy-ethoxy), MOM (—CH$_2$OCH$_3$) moieties, 2,4-dinitrobenzene sulfenyl, tetrahydrofuranyl ether, 3' phosphate, ethers, —F, —H$_2$, —OCH$_3$, —N$_3$, —HCOCH$_3$, and 2-nitrobenzene carbonate.

In the examples shown in FIG. 1B, a linking molecule 16' is attached to the base (e.g., the purine base or the pyrimidine base) of the nucleotide 14'. In some examples, the linking molecule 16' includes a cleavage site, identified by the arrow 42 in FIG. 1B. Some examples of suitable linking molecules 16' are shown in FIG. 1B, although it is to be understood that any suitable cleavable linker may be used that can attach the label 18 to the base or the sugar of the nucleotide 14'.

The label 18 that is included in the labeled nucleotide 12A, 12B, 12C may depend, in part, upon the sensing system 10A-10E or 40A-40B that is to be used with the labeled nucleotide 12A, 12B, 12C. Different labels 18 will be described further in reference to each of the sensing systems 10A-10E and 40A-40B.

Still another example of the labeled nucleotide 12' is shown in FIG. 1C. As depicted in FIG. 1C, the labeled nucleotide 12' includes a nucleotide 14 and a secondary substrate 34 attached to a base or a sugar of the nucleotide 14. Any of the nucleotides 14 or 14' may be used in this case. The secondary substrate 34 may be attached directly to the base or the sugar of the nucleotide 14 or 14'. In one example, the secondary substrate 34 may be attached directly to a carbon atom or a nitrogen atom of the base of the nucleotide 14 or 14'. In another example, the secondary substrate 34 may be attached directly to an oxygen atom or a carbon atom of the sugar molecule of the nucleotide 14 or 14'. If the secondary substrate 34 is attached to the 3' OH of the nucleotide 14 as shown in FIG. 1C, it will block further incorporation of the next base (similar to the labeled nucleotides 12A-12C). This positioning on the sugar molecule may be desirable, because it forces the consumption of the secondary substrate 34 before the next incorporation event and does not require a separate de-blocking agent in order to remove the blocking group. If the nucleotide 14' is used (which includes a 3' OH blocking group 38A, 38B, 38C), the secondary substrate 34 may be attached directly to the 2' position of the sugar molecule of the nucleotide 14'. Alternatively, the secondary substrate 34 may be attached indirectly to the base or the sugar of the nucleotide 14 or 14', for example, through a linking molecule. Examples of suitable linking molecules for attaching the secondary substrate 34 to the base or the sugar of the nucleotide 14 or 14' include a polyethylene glycol chain, an alkyl group, biotin/streptavidin, propargylamino, or any group attached to a commercially available functionalized nucleobase.

In this example labeled nucleotide 12', the secondary substrate 34 is selected so that the kinetics of the consumption of the secondary substrate 34 are at least ten (10) fold faster than kinetics of the polymerase 28 that is used in incorporating the nucleotide base. Thus, the consumption of the secondary substrate 34 occurs faster than the incorporation event, and so the pH change can be detected prior to or as the incorporation event is taking place. In an example, the secondary substrate 34 may be a substrate for a hydrolase, such as a polyester chain (which can be consumed by an esterase), cellulose (which can be consumed by cellulase), a peptide (which can be consumed by a protease), a starch (which can be consumed by an amylase), etc. In another example, the secondary substrate 34 is an additional polyphosphate chain. In this example, the additional polyphosphate chain is not blocked, and its reactivity will be dependent upon a higher local concentration when the nucleotide 12' is reacted upon by the polymerase 28. Also in this example, the terminal phosphate of the nucleotide 14 or 14' may include a blocking group so that the polyphosphate chain of the nucleotide 14 or 14' is not involved in the acid or base generating reaction.

Single Molecule Detection

Referring now to FIG. 2, FIG. 3A, FIG. 3B, FIG. 4, FIG. 5, FIG. 6A and FIG. 6B, each of the sensing systems 10A-10E may be used in single molecule sensing. Each of the systems includes a pH sensor 20, which including two electrodes 22, 24 and a conductive channel 26 connecting the two electrodes 22, 24.

Each pH sensor 20 may be a field effect transistor (FET). In the FET, the electrodes 22, 24 are the source and drain terminals and the conductive channel 26 is the gate terminal. The field effect transistor may be p-channel or n-channel, which affects the polarity of the response but not the sensing principle. Ion sensitive FETs (ISFETs), junction gate FETs (JFETs), metal-semiconductor FETs (MESFETs), metal-oxide-semiconductor FETs (MOSFETs), or junctionless field-effect devices are all suitable detectors in the examples disclosed herein.

The electrodes 22, 24 may comprise any suitable conductive material. Examples of suitable source and drain materials include cobalt, cobalt silicide, nickel, nickel silicide, aluminum, tungsten, copper, titanium, molybdenum, indium tin oxide (ITO), indium zin oxide, gold, platinum, carbon, etc.

The conductive channel 26 may include any electrically conductive or semi-conductive and pH sensitive material. In one example, the conductive channel 26 is an electrically conductive channel. In one example, the electrically conductive or semi-conductive and pH sensitive material is capable of sensing charged ions at its surface. In another example, the electrically conductive or semi-conductive and pH sensitive material includes surface groups, or is coated with another material that includes surface groups that are capable of undergoing protonation and/or deprotonation in response to charged ions generated by the reaction of the secondary substrate 34 with the pH altering moiety. The electrically conductive or semi-conductive and pH sensitive material may comprise an organic material, an inorganic material, or both.

In some examples, the electrically conductive or semi-conductive and pH sensitive material may include a semi-conducting material, such as silicon, that is capable of detecting charge. The semi-conductive and pH sensing material may also have a gate dielectric on at least a portion of its surface. In some examples, the gate dielectric may surround the entire outer surface of the semi-conductive and pH sensing material (except at the contact points with the electrodes 22, 24), and in other examples, the gate dielectric may be positioned on a portion of the outer surface of the semi-conductive and pH sensing material. In one example, the gate dielectric serves to prevent leakage of current into the surrounding environment (e.g., fluid), and may also provide the surface groups that are capable of undergoing protonation and/or deprotonation. Examples of the gate dielectric include silicon dioxide ($SiO_2$), silicon oxynitride (SiON), silicon nitride ($Si_3N_4$), tantalum pentoxide ($Ta_2O_5$), hafnium oxide ($HfO_2$), zirconium oxide ($ZrO_2$), aluminum oxide ($Al_2O_3$), hafnium or zirconium silicates ($HfSiO_4$, $ZrSiO_4$), etc. The surface groups may be silanol groups (Si—OH), Si—$NH_2$ groups, carboxyl groups, (—COOH) or hydroxyl (—OH) groups.

In other examples, the electrically conductive or semi-conductive and pH sensitive material may include a carbon material (e.g., carbon nanotubes, glassy carbon, graphene) without a gate dielectric. These electrically conductive or semi-conductive and pH sensitive materials may include carboxyl (—COOH) groups, hydroxyl (—OH) groups, or other surface functionality that responds to pH or allows pH sensitive functional groups to be attached.

In still other examples, the electrically conductive or semi-conductive and pH sensitive material may be a biomolecule. Examples of suitable biomolecules include peptides and deoxyribonucleic acids. These materials may have a low pKa at the pH generated as a result of the acid or base generating reaction, and thus may also include a conductivity modulator that has a pKa near neutral. For example, the conductivity of peptides may be modulated by pH sensitive amino acids (histidine, etc.). For another example, the conductivity of the DNA may be modulated with a pH responsive intercalator, such as doxorubicin (pKa ~8) and its analogs.

In the single molecule sensing systems 10A-10E, the conductive channel 26 may have any suitable geometry, such as a tubular structure, a wire structure, a planar structure, etc. In some examples, the conductive channel 26 may also be a nanostructure that has at least one dimension on the nanoscale (ranging from 1 nm to less than 1 µm). In one example, this dimension refers to the largest dimension. In an example, the conductive channel 26 of the pH sensor is selected from the group consisting of a semi-conducting nanostructure, a graphene nanostructure, a metallic nanostructure, and a conducting polymer nanostructure. The nanostructure may be a multi- or single-walled nanotube, a nanowire, a nanoribbon, etc.

Each of the sensing systems 10A-10E suitable for use with single molecule sensing includes a polymerase 28 attached to the surface of the conductive channel 26. In some examples, the polymerase 28 alone is attached to the conductive channel 26 (see, e.g., FIG. 2), and in other examples, the polymerase 28 is part of a complex 30A-30D (see, e.g., FIG. 3A, FIG. 3B, FIG. 4, FIG. 5, FIG. 6A and FIG. 6B) that includes another component linked to the polymerase 28.

It is to be understood that the polymerase 28 is capable of holding a template polynucleotide chain, and of incorporating one nucleotide (from a labeled nucleotide 12, 12A, 12B, 12C, or 12') at a time into a nascent strand that is being formed along the template. It is to be understood that the polymerase 28 and its functions are separate and distinct from the acid and base generating reaction(s) involving the secondary substrate 34. In particular, the polymerase 28 participates in a separate acid generating reaction from the acid and base generating reaction(s) involving the secondary substrate 34. For example, the polymerase 28 generates a small amount of acid as a result of nucleotide base incorporation (e.g., 1 molecule per incorporation event), whereas the acid or base generating reaction(s) generates hundreds, or thousands, or even more protons or molecules of base. The acid generated by the polymerase 28 will be overwhelmed by the large amount of acid or base generated from the reaction involving the secondary substrate 34. In some instances, the local pH change resulting from the acid or base generating reactions may affect the kinetics of the polymerase 28. In some instances, the pH change may turn off the polymerase 28 activity until the baseline pH is resumed. This may be advantageous to create a delay between incorporation events (e.g., when the nucleotide 12 or 12' is used). Other factors, such as selection of a pH altering moiety, a buffer, temperature changes during incorporation, etc. may also be adjusted to further enhance or counteract a particular effect on the polymerase kinetics.

Using any of the sensing systems 10A-10E, a method for single molecule sensing includes introducing a template polynucleotide chain 44 (see, e.g., FIG. 2) to a sensor 20 having a polymerase 28 (alone or as part of a complex) tethered to a conductive channel 26; introducing a fluid including a secondary substrate 34 and labeled nucleotides 12, 12A, 12B, 12C, or 12' to the sensor 20, whereby a nucleotide of one of the labeled nucleotides 12, 12A, 12B, 12C, or 12' associates with the polymerase 28 and a label 18 of the one of the labeled nucleotides 12, 12A, 12B, 12C, or 12' participates in a pH altering reaction involving the secondary substrate 34 that is within proximity of the conductive channel 26; and detecting a response of the conductive channel 26. In some instances, the detected change in charge will be relative to a baseline charge. Moreover, the different nucleotides 12, 12A-12C, or 12' may have different incorporation rates, which can affect, for example, how long acid or base is generated or how long the acid or base generating reaction is inhibited. This in turn will affect the local pH level and the charge at the surface of the conductive channel 26. The incorporation rate may be used to distinguish different nucleotides.

Each of the sensing systems 10A-10E and any methods associated with the sensing systems 10A-10E will now be described in more detail with reference to the individual figures in which they are shown.

Sensing System 10A

Referring specifically to FIG. 2, the sensing system 10A includes the pH sensor 20 and the polymerase 28 attached to the conductive channel 26 through a tether 32.

In this example sensing system 10A, any polymerase 28 that can accept the labeled nucleotides 12 or 12A-12C (FIG. 2), and that can successfully incorporate the nucleotide base into the nascent strand 46 along the template 44 may be used. In the single molecule sensing techniques disclosed herein, it is desirable for the polymerase 28 to be highly processive, so that multiple incorporation events may take place. Examples polymerases include those polymerases from family A, such as Bsu Polymerase, Bst Polymerase, Taq Polymerase, T7 Polymerase, and many others; polymerases from families B and B2, such as Phi29 polymerase and other highly processive polymerases (family B2), Pfu Polymerase (family B), KOD Polymerase (family B), 9oN (family B), and many others; polymerases from family C, such as *Escherichia coli* DNA Pol III, and many others, polymerases from family D, such as *Pyrococcus furiosus* DNA Pol II, and many others; polymerases from family X, such as DNA Pol μ, DNA Pol β, DNA Pol σ, and many others. In one example, it may be desirable to select a polymerase 28 that is known to function over at least 2 pH units, which is sufficient to provide a 100 mV range in signal. With four different nucleotides and an "off" state, this range may involve discriminating 20 mV changes, which are detectable.

In this example sensing system 10A, the tether 32 is used as an anchor for the polymerase 28. An example of a suitable tether 32 includes polyethylene glycol (PEG). In the sensing system 10A, the length of the tether 32 is sufficient to hold the polymerase 28 close enough to the channel 26 so that any of the generated acid or base is able to diffuse to the channel 26 before it is neutralized in solution. In an example, the tether 32 may have a length ranging from about 2 nm to about 200 nm, or from about 5 nm to about 150 nm, or from about 10 nm to about 100 nm. In some examples, the tether 32 holds the polymerase 28 at least 10 nm away from the conductive channel 26. This may be desirable, for example, so that conformal changes to the polymerase 28, charges of the polymerase 28, and/or charges of the target/template polynucleotide chain held by the polymerase 28 do not interfere with the sensing operation of the pH sensor 20. However, it is to be understood that this example minimal distance (at least 10 nm) may not be needed, for example, when the pH changes dominate the signal that is sensed.

While not shown, the sensing system 10A may also include a detector to detect voltage and/or current changes that correspond with the pH change taking place at or near the surface of the pH sensing channel 26.

Also while not shown, the sensing system 10A may be positioned on a support, such as a silicon chip or a complementary metal-oxide semiconductor (CMOS). The electrodes 22, 24 may be connected to electronic circuitry that enables their operation (e.g., once hooked up to a detector and power supply).

In some examples, the sensor 10A may come pre-assembled.

In other examples, the sensor components may be part of a kit, and the kit components may be used to assemble the sensor 10A. An example of the kit includes the pH sensor 20 on the support, and a separate polymerase solution. The polymerase solution includes a liquid carrier and any example of the polymerase 28. In some examples, the polymerase 28 is attached to the tether 32, and in other examples, the tether 32 is attached to the pH sensing channel 26 as part of the sensing system 10A. As examples, the liquid carrier of the polymerase solution may be water, or an ionic salt buffer fluid, such as saline citrate at milli-molar to molar concentrations.

When using the kit, a user can deposit the polymerase solution on the support, and allow the polymerase solution to remain on the support for a suitable time for the tether 32 to attach to the conductive channel 26, or for the polymerase 28 to attach to the tether 32 on the conductive channel 26. The support may be rinsed with a suitable buffer to remove any non-bound polymerase 28.

In FIG. 2, examples of the kit may also include a fluid that is to be used with the sensor 10A during single molecule sensing. This fluid includes a liquid carrier, labeled nucleotides 12 or 12A-12C, and the secondary substrate 34. In some instances, this fluid also includes a template polynucleotide chain 44. In other instances, one solution includes the liquid carrier, the labeled nucleotides 12 or 12A-12C, and the secondary substrate 34, and another solution includes the template polynucleotide chain 44.

The template polynucleotide chain 44 may be any sample that is to be sequenced, and may be composed of DNA, RNA, or analogs thereof (e.g., peptide nucleic acids). The template polynucleotide chain 44 may be a circular template. The source of the template (or target) polynucleotide chain 44 can be genomic DNA, messenger RNA, or other nucleic acids from native sources. In some cases, the template polynucleotide chain 44 that is derived from such sources can be amplified prior to use in a method or system disclosed herein. Any of a variety of known amplification techniques can be used including, but not limited to, polymerase chain reaction (PCR), rolling circle amplification (RCA), multiple displacement amplification (MDA), or random primer amplification (RPA). It is to be understood that amplification of the template polynucleotide chain 44 prior to use in the method or system set forth herein is optional. As such, the template polynucleotide chain 44 will not be amplified prior to use in some examples. Template/target polynucleotide chains 44 can optionally be derived from synthetic libraries. Synthetic nucleic acids can have native DNA or RNA compositions or can be analogs thereof.

The labeled nucleotides 12 or 12A-12C include any example of the nucleotide 14 or 14' and the linking molecule 16 or 16' disclosed herein. The label 18 of the labeled nucleotide 12 or 12A-12C shown in FIG. 2 is a catalyst label 18A. As used herein, the "catalyst label" refers to a chemical species that initiates or accelerates an acid or base generating reaction involving the secondary substrate 34. As such, the catalyst label 18A is one example of a pH altering moiety that is attached to the labeled nucleotide 12 or 12A-12C. For example, the catalyst label 18A may be an enzyme that reacts with the secondary substrate 34 to generate an acid, thereby lowering the pH. A specific example of an acid generating pair includes acetylcholinesterase as the catalyst label 18A and an ester substrate (e.g., acetylcholine) as the secondary substrate 34. Another specific example of an acid generating pair includes carbonic anhydrase as the catalyst label 18A and a bicarbonate ion as the secondary substrate 34. For another example, the catalyst label 18A may be an enzyme that reacts with the secondary substrate 34 to generate a base, thereby increasing the pH. In some examples, the surface groups at the surface of the channel 26 are sensitive to the acidic or basic ions that are generated, and can undergo protonation or deprotonation, thereby altering the charge density directly on the channel 26 surface. In other examples, the charged ions generated during the acid generating or base generating reactions are sensed by the conductive channel 26.

The liquid carrier of the fluid that may be used with the sensor 10A during single molecule sensing is water or a low buffer fluid (10 mM or less) having a pH ranging from about 6 to about 9, or from about 7 to about 8. The pH of the fluid depends upon the polymerase 28 that is used and any conditions that help to maximize the signal when there is a pH change. Because the catalyst label 18A and the secondary substrate 34 are both present in the fluid in this example, some acid or base generating reaction(s) may take place in the fluid away from the conductive channel 26. However, the ions generated in these reaction(s) may be neutralized in the fluid (by the low buffer fluid), and thus may not result in a detectable signal. This prevents large global pH changes in the fluid. It is to be understood, however, that when the labeled nucleotide 12 or 12A-12C is held by the polymerase 28, the catalyst label 18A is held closer in proximity to the pH sensing channel 26 (e.g., as compared to when the labeled nucleotide 12 or 12A-12C is floating in the solution). In turn, any pH change resulting from a reaction involving the secondary substrate 34 and the temporarily bound catalyst label 18A is also closer in proximity to the pH sensing channel 26. Moreover, the kinetics of the catalyst label 18A may be faster than the kinetics of the polymerase 28. For example, the turnover frequency of the acid generating enzyme, acetylcholinesterase, may be as high as $25,000 \, s^{-1}$, while an incorporation event may take anywhere from about $0.1 \, s^{-1}$ to about $100 \, s^{-1}$. In this example, the catalyst label 18A may generate from about 250 to about 250,000 molecules of acid per nucleotide that is incorporated (per a single incorporation event). When the catalyst label 18A and the acid or base generation are localized at the surface of the conductive channel 26, a pH gradient may be generated around the pH sensing channel 26, which can generate detectable charge signals at the pH sensing channel 26. These signals can be recorded.

In an example, the buffer concentration in the low buffer fluid may be less than about 10 mM, which, as described herein, can prevent global pH changes, but can allow local pH changes near the conductive channel 16 to be detected. In some instances, the buffer concentration is significantly less than 10 mM, examples of which include about 5 mM, about 2.5, mM, about 2 mM, about 1 mM, about 0.5 mM, or about 0.25 mM. In other examples, solid phase buffers may be used to help maintain a global pH without buffering the local environment.

In one example of the fluid that may be used with the sensing system 10A, four different labeled nucleotides 12 or 12A-12C may be included. The four different labeled nucleotides 12 or 12A-12C include distinct nucleotides 14 or 14' (e.g., T, A, G or C) and distinct catalyst labels 18A. The distinct catalyst labels 18A may possess different kinetics, so that the acid or base is generated at different rates, which in turn, will result in different charge densities at the channel 26. Because the distinct catalyst labels 10A are nucleotide-specific (e.g., a specific label 18A is selected for a specific base), the response of the pH sensor 20 may be indicative of the incorporated base of the labeled nucleotide 12 or 12A-12C.

The following description relates to an example method that involves the labeled nucleotides 12 and the sensing system 10A. In this example, the template polynucleotide chain 44 may be introduced to the sensing system 10A in a fluid, such as a biologically stable solution, together with or separate from the labeled nucleotides 12 and the secondary substrate 34. The polymerase 28 associates with the template polynucleotide chain 44, so that the chain 44 is held in place. A complementary base of one of the labeled nucleotides 12 will be incorporated into a nascent strand 46 (that is being formed along the template polynucleotide chain 44) by the polymerase 28. During the incorporation event, the catalyst label 18A of the labeled nucleotide 12 is brought into proximity of the channel 26 and any secondary substrate 34 in the fluid that is also within proximity of the channel 26. Because the kinetics of the catalyst label 18A may be faster than the incorporation event, the acid or base generating reaction with the secondary substrate 34 takes place before the incorporation of the base is complete. The charged ions from the acid or base generating reaction may be detected at the conductive channel 26, or, if reactive surface groups are present, may react with the surface groups to alter the charge state of the surface groups. The altered charge is detected by the pH sensor 20.

In this example method, after incorporation of the nucleotide base into the nascent strand 46, the bond between the alpha phosphate and the linking molecule 16 or between the alpha phosphate and beta phosphate is naturally cleaved. This natural cleavage enables the label 18A (and the linking molecule 16) to dissociate from the incorporated nucleotide base and diffuse away from the sensing system 10A. The polymerase 28 can then receive another labeled nucleotide 12 which includes a nucleotide base that is complementary to the next nucleotide in the template polynucleotide chain 44.

The following description relates to an example method that involves the labeled nucleotides 12A-12C and the sensing system 10A. In this example, the template polynucleotide chain 44 may be introduced to the sensing system 10A in a fluid, such as a biologically stable solution, together with or separate from the labeled nucleotides 12A-12C and the secondary substrate 34. The polymerase 28 associates with the template polynucleotide chain 44, so that the chain 44 is held in place. A complementary base of one of the labeled nucleotides 12A-12C will be incorporated into a nascent strand 46 (that is being formed along the template polynucleotide chain 44) by the polymerase 28. In this example, the labeled nucleotide 12A-12C includes a reversible terminator. As such, incorporation of the labeled nucleotide 12A-12C serves as a terminator for polymerization. This enables acid or base generation and charge detection to take place in a similar manner as described above.

In this example method, after incorporation of the nucleotide base into the nascent strand 46, the fluid, which includes any non-incorporated nucleotides, may be removed from the sensing system 10A. This may be accomplished using a washing solution (e.g., water). A de-blocking agent may then be introduced into the sensing system 10A. The de-blocking agent may be capable of i) cleaving any cleavable linking molecules 16' from the incorporated labeled nucleotide 12A-12C (which also removes the catalyst label 18A) and ii) removing the 3' OH blocking group 38A, 38B, 38C (see FIG. 1B) from the incorporated labeled nucleotide 12A-12C. Removal of the 3' OH blocking group 38A, 38B, 38C enables a subsequent sequencing cycle to be performed. Examples of 3' OH blocking groups and suitable de-blocking agents include: o-nitrobenzyl ethers and alkyl o-nitrobenzyl carbonate that can be removed photolytically; ester moieties that can be removed by base hydrolysis; allyl-moieties that can be removed with NaI, chlorotrimethylsilane and $Na_2S_2O_3$ or with Hg(II) in acetone/water; azidomethyl which can be cleaved with phosphines, such as tris(2-carboxyethyl)phosphine (TCEP) or tri(hydroxypropyl)phosphine (THP); acetals, such as tert-butoxy-ethoxy which can be cleaved with acidic conditions; MOM ($—CH_2OCH_3$) moieties that can be cleaved with $LiBF_4$ and $CH_3CN/H_2O$; 2,4-dinitrobenzene sulfenyl which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g., polynucleotide kinase). Other useful reversible moieties include ethers, $—F$, $—H_2$, $—OCH_3$, $—N_3$, $—HOOCH_3$, and 2-nitrobenzene carbonate, and useful de-blocking treatments include irradiation with light (e.g., to induce photocleavage), heating, exposure to chemical reactants, exposure to catalysts, exposure to electrical current (e.g., to induce electrolysis), or the like.

Sensing System 10B

Figure 3A:
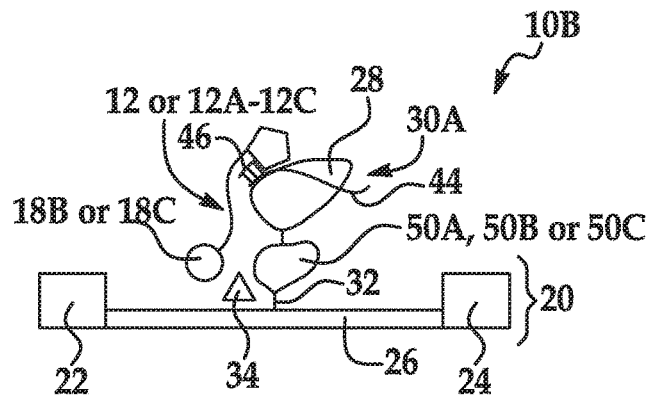
FIG. 3A is a schematic illustration depicting another example of the sensing system disclosed herein, and an example of labeled nucleotides and a secondary substrate that may be used with this example of the sensing system.
Figure 3B:
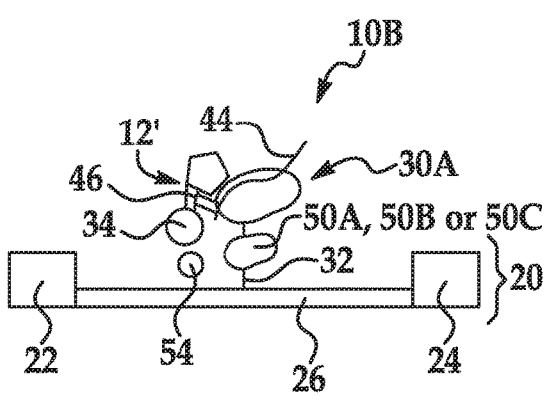
FIG. 3B depicts the example of the sensing system of FIG. 3A in use with another example of the labeled nucleotide disclosed herein.

Referring specifically to FIG. 3A and FIG. 3B, the sensing system 10B includes the pH sensor 20 and a complex 30A attached to the conductive channel 26 of the pH sensor 20.

The complex 30A includes the polymerase 28 linked to a pH altering moiety (shown, in these examples as 50A, 50B, or 50C) that is to participate in generating a pH change within proximity of the conductive channel 26 from consumption of a secondary substrate 34 in a fluid that is exposed to the pH sensor 20.

The polymerase 28 of the complex 30A may be any example of the polymerase described in reference to FIG. 2.

In this example, the pH altering moiety is selected from the group consisting of an enzyme 50A, a co-factor 50B, and an activator 50C.

The enzyme 50A generates an acid or base in a reaction with the secondary substrate 34. As examples, the enzyme 50A may be selected from the group consisting of hydrolases and oxidases. Examples of suitable hydrolases include phosphatases, esterases (e.g., acetylcholinesterase), sequence specific proteases (e.g., TEV protease or thrombin), and glycosidases (that do not degrade the ribose, such as cellulose or amylase). Another suitable hydrolase is carbonic anhydrase. Examples of suitable oxidases include glucose oxidase, monoamine oxidase, xanthine oxidase, etc. While several examples have been provided, it is believed that any available enzyme 50A or engineered enzyme 50A may be used, as long as the enzyme kinetics are faster than the polymerase kinetics.

The co-factor 50B is a substance whose presence is essential for the activity of an enzyme that generates an acid or base in a reaction with the secondary substrate 34. Some examples of suitable co-factors 50B for oxidases include flavin adenine dinucleotide (FAD), nicotine adenine dinucleotide (NAD), nicotine adenine dinucleotide phosphate (NADP), etc.

The activator 50C is a substance that initiates or stimulates the acid or base generating reaction with the secondary substrate 34. In some instances, the activator 50C functions similarly to the co-factor 50B, and thus any examples of the co-factor 50B may be used for the activator 50C. For metal-dependent hydrolases, examples of suitable activators 50C include divalent metals.

In the complex 30A, the polymerase 28 and any example of the pH altering moiety 50A-50C are conjugated together. In one example, this complex 30A is a fusion protein or a protein chimera. The complex 30A may be formed using conjugation methods, such as a spytag-spycatcher coupling reaction, a π-clamp mediated cysteine conjugation, biotin/streptavidin, a SUMO (small ubiquitin-like modifier) protein, His6/NTA chelation with the metal, cysteine/maleimide, dibenzocyclooctyne (DBCO)/azide, or any other suitable conjugation method.

The complex 30A may be attached to the conductive channel 26 through a tether 32, examples of which are described in reference to FIG. 2. Alternatively, the complex 30A may be directly attached via bonding between the pH altering moiety 50A-50C and groups at the surface of the conductive channel 26.

While not shown, the sensing system 10B may also include a detector to detect voltage and/or current changes that correspond with the pH change taking place at or near the surface of the pH sensing channel 26.

Also while not shown, the sensing system 10B may be positioned on a support, such as a silicon chip. The electrodes 22, 24 may be connected to electronic circuitry that enables their operation (e.g., once hooked up to a detector and power supply).

In some examples, the sensor 10B may come pre-assembled.

In other examples, the sensor components may be part of a kit, and the kit components may be used to assemble the sensor 10B. An example of the kit includes the pH sensor 20 on the support, and a fluid that is used to introduce the complex 30A to the pH sensor 20. The fluid includes a liquid carrier and the complex 30A. In some examples, the complex 30A in the fluid is attached to the tether 32. In other examples, the tether 32 is attached to the pH sensing channel 26 as part of the sensing system 10B. In still other examples where there is a direct bond formed between the pH altering moiety 50A-50C and the surface groups of the channel 26, it is to be understood that the complex 30A in the fluid is not attached to the tether 32, and the tether 32 is not attached to the pH sensing channel 26. In an example, the liquid carrier is water or an example of the low buffer fluid, such as saline citrate at milli-molar concentrations.

In one example of this kit, the complex 30A in the liquid carrier includes the polymerase 28 linked to the at least one enzyme 50A. In another example of this kit, the complex 30A in the liquid carrier includes the polymerase 28 conjugated to the co-factor 50B. In still another example of this kit, the complex 30A in the liquid carrier includes the polymerase 28 conjugated to the activator 50C. In each of these examples, the complex 30A may also include the tether 32. When using these examples of the kit, a user can deposit the fluid on the support, and allow the fluid to remain on the support for a suitable time for the tether 32 to attach the complex 30A to the conductive channel 26, for the complex 30A to attach to a tether 32 on the channel 26, or for the pH altering moiety 50A-50C to bond to the surface groups of the channel 26. The support may be rinsed with a suitable buffer to remove any non-bound complexes 30A.

Some examples of the kit may also include fluid(s) that is/are to be used with the sensing system 10B during single molecule sensing. The contents of the fluid(s) may vary, depending upon which pH altering moiety 50A-50C is part of the complex 30A of the sensing system 10B and which labeled nucleotides 12, 12A-12C, or 12' are used. Several examples of these fluid(s) will now be described.

In the examples shown in FIG. 3A, the fluid(s) to be used during single molecule sequencing include any example of the liquid carrier disclosed herein, the labeled nucleotides 12 or 12A-12C, and the secondary substrate 34 (which, in these examples, is a separate molecule from the labeled nucleotides 12 or 12A-12C).

The label 18B or 18C that is attached to the labeled nucleotides 12 or 12A-12C will depend upon which pH altering moiety is included in the complex 30A.

When the sensing system 10B includes the enzyme 50A as part of the complex 30A, the label 18B is used. As mentioned herein, the enzyme 50A generates an acid or base in a reaction with the secondary substrate 34 when the two are within proximity of one another. To correlate the acid or base generating reaction between the enzyme 50A and the secondary substrate 34 with the incorporated labeled nucleotide 12 or 12A-12C, the label 18B on the labeled nucleotides 12 or 12A-12C may be tailored to enhance the kinetics of the enzyme 50A or slow the kinetics of the enzyme 50A. As such, the label 18B is one example of a pH altering moiety that is attached to the labeled nucleotide 12 or 12A-12C. This example of the system 10B thus includes two different examples of the pH altering moiety. Thus, in one example, the label 18B is selected from the group consisting of a first group that enhances kinetics of the enzyme 50A and a second group that slows kinetics of the enzyme 50A.

When the label 18B enhances the kinetics of the enzyme 50A, it also enhances (e.g., initiates or speeds up) the kinetics of the acid or base generating reaction involving the enzyme 50A and the secondary substrate 34. Examples of labels 18B that enhance the kinetics of the enzyme 50A include co-factors of the enzyme. Examples of other labels 18B that enhance the kinetics of the enzyme 50A include those that have a crowding effect. This type of label 18B may be a large crowding agent that can reduce the volume of water available for other molecules and effectively increase the local concentration of the secondary substrate 34 (which, in turn, increases the speed of the reaction).

In contrast, when the label 18B slows the kinetics of the enzyme 50A, it also slows the kinetics of the acid or base generating reaction involving the enzyme 50A and the secondary substrate 34. Examples of labels 18B that slow the kinetics of the enzyme 50A may be selected from the group consisting of an allosteric inhibitor, a steric exclusion group, and a buffering group. An allosteric inhibitor binds to an allosteric site of the enzyme 50A, and alters the conformation of an active site of the enzyme 50A. As a result, the enzyme 50A is no longer able to react with the secondary substrate 34 and becomes inactive. It may be desirable for the binding between the allosteric inhibitor and the enzyme 50A to be weaker than the binding between the polymerase 28 and the base of the labeled nucleotide 12 or 12A-12C so that labeled nucleotides 12 or 12A-12C are not bound only by the label 18B. A steric exclusion group may be a molecule that is bulkier than the secondary substrate 34. The steric exclusion group of an incorporated labeled nucleotide can block the secondary substrate 34 from getting close enough to the enzyme 50A to react. In other words, the steric exclusion group may reduce access to the enzyme 50A without actually binding to the enzyme 50A. A buffering group may act as a local buffer to absorb the protons generated during an acid generating reaction or the molecules of base generated during a base generating reaction, and thereby neutralize the pH. As an example, dendrimers possessing multiple acid or base groups may serve to buffer the local vicinity of the conductive channel 26.

In an example, the labels 18B that are attached to different nucleotides 12 or 12A-12C (e.g., A, T, C, G) may be selected to increase or decrease acid or base generation at different rates. In this example, when one of the labeled nucleotide 12 or 12A-12C is being incorporated by the polymerase 28, the label 18B is brought within proximity of the enzyme 50A and the secondary substrate 34, and enhances or slows the reaction at a unique, label-dependent rate. In turn, the pH at the conductive channel 26 is altered. The change in pH correlates with increased or decreased acid or base generation, and thus can be used to identify the incorporated labeled nucleotide 12 or 12A-12C.

When the sensing system 10B includes the co-factor 50B or the activator 50C as part of the complex 30A, the label 18C is used. The label 18C may be the enzyme that generates an acid or base in a reaction with the secondary substrate 34. As such, the label 18C is one example of a pH altering moiety that is attached to the labeled nucleotide 12 or 12A-12C. This example of the system 10B thus includes two different examples of the pH altering moiety. When the labeled nucleotide 12 or 12A-12C is incorporated by the polymerase 28, the enzyme label 18C is brought within proximity of the co-factor 50B or the activator 50C and the secondary substrate 34. The attached co-factor 50B or activator 50C can enhance or initiate the reaction between the enzyme label 18C and the secondary substrate 34 in the fluid.

Because the labeled nucleotides 12 or 12A-12C do not include the secondary substrate 34, the fluid(s) represented in the example of FIG. 3A also include the secondary substrate 34. The secondary substrate 34 may be any secondary substrate 34 that can react with the enzyme 50A to generate an acid or base, or whose reaction with the enzyme label 18C can be enhanced or initiated by the co-factor 50B or the activator 50C.

The following description relates to an example method that involves the labeled nucleotides 12 and the sensing system 10B. In this example, the template polynucleotide chain 44 may be introduced to the sensing system 10B in a fluid, such as a biologically stable solution, together with or separate from the labeled nucleotides 12 and the secondary substrate 34. The polymerase 28 associates with the template polynucleotide chain 44, so that the chain 44 is held in place. A complementary base of one of the labeled nucleotides 12 will be incorporated into a nascent strand 46 (that is being formed along the template polynucleotide chain 44) by the polymerase 28. During the incorporation event, the label 18B or 18C of the labeled nucleotide 12 is brought into proximity of the channel 26, the pH altering moiety 50A-50C, and any secondary substrate 34 in the fluid that is also within proximity of the pH altering moiety 50A-50C. The acid or base generating reaction with the secondary substrate 34 may be enhanced, slowed down, or inhibited depending upon the complex 30A and labels 18B or 18C that are used, which alters the pH of the fluid, and the charge, at the channel 26 surface. In this example method, after incorporation of the nucleotide base into the nascent strand 46, the bond between the alpha phosphate and the linking molecule 16 or between the alpha phosphate and beta phosphate is naturally cleaved. This natural cleavage enables the label 18B or 18C (and the linking molecule 16) to dissociate from the incorporated nucleotide base and diffuse away from the sensing system 10B. The polymerase 28 can then receive another labeled nucleotide 12 which includes a nucleotide base that is complementary to the next nucleotide in the template polynucleotide chain 44.

The following description relates to an example method that involves the labeled nucleotides 12A-12C and the sensing system 10B. In this example, the template polynucleotide chain 44 may be introduced to the sensing system 10B in a fluid, such as a biologically stable solution, together with or separate from the labeled nucleotides 12A-12C and the secondary substrate 34. The polymerase 28 associates with the template polynucleotide chain 44, so that the chain 44 is held in place. A complementary base of one of the labeled nucleotides 12A-12C will be incorporated into a nascent strand 46 (that is being formed along the template polynucleotide chain 44) by the polymerase 28. The acid or base generating reaction with the secondary substrate 34 may be enhanced, slowed down, or inhibited depending upon the complex 30A and labels 18B or 18C that are used, which alters the pH of the fluid, and the charge, at the channel 26 surface. In this example, the labeled nucleotide 12A-12C includes a reversible terminator. As such, incorporation of the labeled nucleotide 12A-12C serves as a terminator for polymerization. This enables the enhanced, slowed down, or inhibited acid or base generation and charge detection to take place in a similar manner as described above. In this example method, washing and exposure to a de-blocking agent may be used to prepare the sensing system 10B for another sequencing cycle.

In any of the examples described in reference to FIG. 3A, it is to be understood that the distance between the polymerase 28 and the pH altering moiety 50A-50C and the length of the linking molecule 16, 16' may be selected so that the label 18B or 18C is brought within proximity of the pH altering moiety 50A-50C when its labeled nucleotide 12 or 12A-12C is being incorporated by the polymerase 28. This enables predictable effects on the acid or base generating reaction.

As mentioned herein, the sensing system 10B may also be used with the labeled nucleotide 12', which, as described in reference to FIG. 1C, includes the secondary substrate 34 attached to the nucleotide 14. FIG. 3B illustrates the system 10B and the labeled nucleotide 12'.

In this example, the fluid in the kit includes the labeled nucleotides 12', rather than the labeled nucleotides 12 or 12A-12C. Unlike the fluids described in reference to FIG. 3A, this fluid does not include a separate secondary substrate 34 because the secondary substrate 34 is attached to the nucleotide 14.

When the sensing system 10B includes the enzyme 50A as part of the complex 30A, the fluid exposed to the system 10B may include the liquid carrier and the labeled nucleotides 12'. When the polymerase 28 incorporates the base of the labeled nucleotides 12', the secondary substrate 34 is brought within proximity of the enzyme 50A, and the acid or base generating reaction may take place.

When the sensing system 10B includes the co-factor 50B or the activator 50C as part of the complex 30A, the fluid exposed to the system 10B may include the liquid carrier and the labeled nucleotides 12'. This example of the kit may also include an enzyme fluid that is separate from the fluid containing the labeled nucleotides 12'. The enzyme fluid is included because neither the labeled nucleotide 12' nor the complex 30A contains the enzyme that participates in the acid or base generating reaction with the secondary substrate 34. The enzyme fluid may include a liquid carrier (e.g., any of the buffers disclosed herein) and an enzyme 54 that is to participate in the consumption of the secondary substrate 34. The enzyme 54 used depends on the secondary substrate 34 that is attached to the labeled nucleotide 12'.

When the fluid(s) containing the template polynucleotide chain 44 and the labeled nucleotide 12', and, in some instances, the enzyme fluid, are introduced (sequentially or simultaneously) to the sensing system 10B, the template polynucleotide chain 44 associates with the polymerase 28 and a complementary one of the labeled nucleotides 12' is incorporated into the growing nascent strand 46. In this example, the enzyme 50A of the complex 30A or the free floating enzyme 54 will react to consume the secondary substrate 34 to generate the acid or base, and this reaction will be faster than the nucleotide incorporation. In these examples, the secondary substrate 34 is consumed, and upon its consumption, the pH will return to the baseline level and the nucleotide base will be incorporated.

Sensing System 10C

Figure 4:
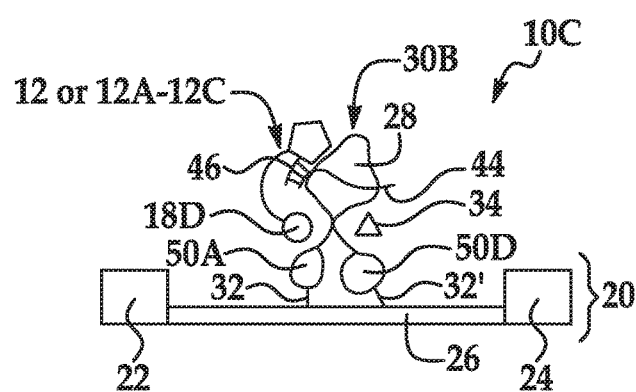
FIG. 4 is a schematic illustration depicting another example of the sensing system disclosed herein, and an example of a labeled nucleotide and a secondary substrate that may be used with this example of the sensing system.

Referring specifically to FIG. 4, the sensing system 10C includes the pH sensor 20 and a complex 30B attached to the conductive channel 26 of the pH sensor 20.

The complex 30B includes the polymerase 28 attached to two different enzymes 50A and 50D. The polymerase 28 of the complex 30A may be any example of the polymerase described in reference to FIG. 2.

The enzymes 50A, 50D may be any example of the enzyme described in reference to FIG. 3A and FIG. 3B, as long as the two enzymes 50A, 50D are different. Each of the enzymes 50A and 50D generates an acid or base in a reaction with the secondary substrate 34; however, the enzymes 50A and 50D may be selected so that they have a different response when in proximity of a particular nucleotide label 18D. As one example, the enzyme 50A may respond to the respective labels 18D attached to two types of labeled nucleotides 12 or 12A-12C (e.g., A and T), and may not respond to the respective labels 18D attached to the other two types of labeled nucleotides 12 or 12A-12C (e.g., C and G). Conversely, the enzyme 50D may respond to the respective labels 18D attached to the other two types of labeled nucleotides 12 or 12A-12C (e.g., C and G), but may not respond to the respective labels 18D attached to the two types of labeled nucleotides 12 or 12A-12C (e.g., A and T). In this example, each label 18D respectively attached to the nucleotides 12 or 12A-12C may be different from each other label 18D respectively attached to the other nucleotides 12 or 12A-12C.

In the complex 30B, the polymerase 28 and the two different enzymes 50A, 50D are conjugated together. In one example, this complex 30B is a fusion protein or a protein chimera. The complex 30B may be formed using conjugation methods, such as a spytag-spycatcher coupling reaction, a π-clamp mediated cysteine conjugation, biotin/streptavidin, a SUMO (small ubiquitin-like modifier) protein, His6/NTA chelation with the metal, cysteine/maleimide, dibenzocyclooctyne (DBCO)/azide, or any other suitable conjugation method.

In one example (as shown in FIG. 4), the complex 30B may be attached to the conductive channel 26 through tethers 32, 32' attached to each of the enzymes 50A, 50D. In another example, a single tether 32 may attach the polymerase 28 to the conductive channel 26, and the enzymes 50A, 50D may be respectively attached to the polymerase 28. In still another example, there are no tethers 32, 32', but rather, one or both of the enzymes 50A, 50D may form a bond directly with the surface groups of the conductive channel 26 and with the polymerase 28.

While not shown, the sensing system 10C may also include a detector to detect voltage and/or current changes that correspond with the pH change taking place at or near the surface of the pH sensing channel 26.

Also while not shown, the sensing system 10C may be positioned on a support, such as a silicon chip. The electrodes 22, 24 may be connected to electronic circuitry that enables their operation (e.g., once hooked up to a detector and power supply).

In some examples, the sensor 10C may come pre-assembled.

In other examples, the sensor components may be part of a kit, and the kit components may be used to assemble the sensor 10C. An example of the kit includes the pH sensor 20 on the support, and a fluid that is used to introduce the complex 30B to the pH sensor 20. The fluid includes a liquid carrier and the complex 30B. In some examples, the complex 30B in the fluid is attached to the tethers 32, 32'. In other examples, the complex 30B in the fluid includes a single tether 32 attached to the polymerase 28, and the enzymes 50A and 50D are attached to the polymerase 28. In still some other examples, the tether(s) 32, 32' is/are attached to the pH sensing channel 26 as part of the sensing system 10C. In still other examples where there is a direct bond formed between the enzymes 50A, 50D and the surface groups of the channel 26, it is to be understood that the complex 30B in the fluid is not attached to the tethers 32, 32' and the tethers 32, 32' are not attached to the pH sensing channel 26. In an example, the liquid carrier is water or an example of the low buffer fluid, such as saline citrate at milli-molar concentrations.

When using these examples of the kit, a user can deposit the fluid on the support, and allow the fluid to remain on the support for a suitable time for the tethers 32, 32' to attach the complex 30B to the conductive channel 26, for the tether 32 to attach the polymerase 28 of the complex 30B to the conductive channel 26, or for the enzymes 50A and 50D to bond to the surface groups of the channel 26. The support may be rinsed with a suitable buffer to remove any non-bound complexes 30B.

Some examples of the kit may also include fluid(s) that is/are to be used with the sensing system 10C during single molecule sensing. In this example, the fluid(s) included any example of the liquid carrier disclosed herein, the labeled nucleotides 12 or 12A-12C, and the secondary substrate 34 (which, in these examples, is a separate molecule from the labeled nucleotides 12 or 12A-12C).

The label 18D that is attached to the labeled nucleotides 12 or 12A-12C will depend upon the two enzymes 50A, 50D of the complex 30B. As mentioned herein, each of the enzymes 50A, 50D generates an acid or base in a reaction with the secondary substrate 34. To correlate a particular acid or base generating reaction between the enzyme 50A and the secondary substrate 34 or between the enzyme 50D and the secondary substrate 34, each label 18D on the labeled nucleotides 12 or 12A-12C may be tailored to enhance (e.g., initiate or speed up) the kinetics of the enzyme 50A or of the enzyme 50D, or slow the kinetics of the enzyme 50A or of the enzyme 50D. As such, the label 18D is one example of a pH altering moiety that is attached to the labeled nucleotide 12 or 12A-12C. This example of the system 10B thus includes two different examples of the pH altering moiety. Any of the labels 18B may be used for the labels 18D, and each of the four nucleotides (e.g., A, T, C, G) may be labeled with a different label that affects the acid or base generating reactions differently. In one example, the label 18D selected for the labeled nucleotide 12 or 12A-12C with "A" as the nitrogenous base may enhance acid generation at a first rate when in proximity of the enzyme 50A and the secondary substrate 34; the label 18D selected for the labeled nucleotide 12 or 12A-12C with "T" as the nitrogenous base may slow down acid generation at a second rate when in proximity of the enzyme 50A and the secondary substrate 34; the label 18D selected for the labeled nucleotide 12 or 12A-12C with "C" as the nitrogenous base may enhance base generation at a third rate when in proximity of the enzyme 50D and the secondary substrate 34; and the label 18D selected for the labeled nucleotide 12 or 12A-12C with "G" as the nitrogenous base may slow down base generation at a fourth rate when in proximity of the enzyme 50A and the secondary substrate 34. When the different labeled nucleotides are incorporate into the nascent strand 46, different pH levels will result locally at the surface of the charge sensitive channel 46.

Because the labeled nucleotides 12 or 12A-12C do not include the secondary substrate 34, the fluid(s) represented in the example of FIG. 4 also include the secondary substrate 34. The secondary substrate 34 may be any secondary substrate 34 that can react with the enzyme 50A or 50D to generate an acid or base.

The following description relates to an example method that involves the labeled nucleotides 12 and the sensing system 10C. In this example, the template polynucleotide chain 44 may be introduced to the sensing system 10C in a fluid, such as a biologically stable solution, together with or separate from the labeled nucleotides 12 and the secondary substrate 34. The polymerase 28 associates with the template polynucleotide chain 44, so that the chain 44 is held in place. A complementary base of one of the labeled nucleotides 12 will be incorporated into a nascent strand 46 (that is being formed along the template polynucleotide chain 44) by the polymerase 28. During the incorporation event, the label 18D of the labeled nucleotide 12 is brought into proximity of the channel 26, the enzymes 50A and 50D, and any secondary substrate 34 in the fluid that is also within proximity of the enzymes 50A and 50D. The acid or base generating reaction with the secondary substrate 34 may be enhanced, slowed down, or inhibited depending upon the label 18D and its effect on the reaction involving enzyme 50A or 50D. This alters the pH of the fluid, and the charge, at the channel 26 surface. In this example method, after incorporation of the nucleotide base into the nascent strand 46, the bond between the alpha phosphate and the linking molecule 16 or between the alpha phosphate and beta phosphate is naturally cleaved. This natural cleavage enables the label 18D (and the linking molecule 16) to dissociate from the incorporated nucleotide base and diffuse away from the sensing system 10C. The polymerase 28 can then receive another labeled nucleotide 12 which includes a nucleotide base that is complementary to the next nucleotide in the template polynucleotide chain 44.

The following description relates to an example method that involves the labeled nucleotides 12A-12C and the sensing system 10C. In this example, the template polynucleotide chain 44 may be introduced to the sensing system 10C in a fluid, such as a biologically stable solution, together with or separate from the labeled nucleotides 12A-12C and the secondary substrate 34. The polymerase 28 associates with the template polynucleotide chain 44, so that the chain 44 is held in place. A complementary base of one of the labeled nucleotides 12A-12C will be incorporated into a nascent strand 46 (that is being formed along the template polynucleotide chain 44) by the polymerase 28. The acid or base generating reaction with the secondary substrate 34 may be enhanced, slowed down, or inhibited depending upon the label 18D and its effect on the reaction involving enzyme 50A or 50D. This alters the pH of the fluid, and the charge, at the channel 26 surface. In this example, the labeled nucleotide 12A-12C includes a reversible terminator. As such, incorporation of the labeled nucleotide 12A-12C serves as a terminator for polymerization. This enables the enhanced, slowed down, or inhibited acid or base generation and charge detection to take place in a similar manner as described above. In this example method, washing and exposure to a de-blocking agent may be used to prepare the sensing system 10C for another sequencing cycle.

In any of the examples described in reference to FIG. 4, it is to be understood that the distance between the polymerase 28 and the respective enzymes 50A, 50D and the length of the linking molecule 16, 16' may be selected so that the label 18D is brought within proximity of the enzyme 50A and/or and 50D when its labeled nucleotide 12 or 12A-12C is being incorporated by the polymerase 28. This enables predictable effects on the acid or base generating reaction.

Sensing System 10D

Figure 5:
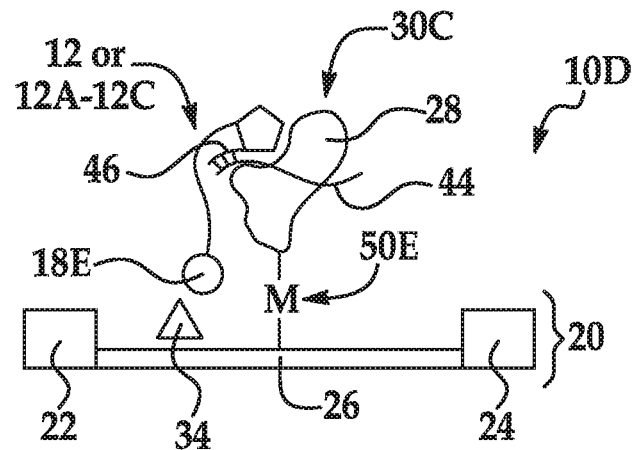
FIG. 5 is a schematic illustration depicting still another example of the sensing system disclosed herein, and an example of a labeled nucleotide and a secondary substrate that may be used with this example of the sensing system.

Referring specifically to FIG. 5, the sensing system 10D includes the pH sensor 20 and a complex 30C attached to the conductive channel 26 of the pH sensor 20.

The complex 30C includes the polymerase 28 linked to a metal coordination complex ("M") that is to create a pH change within proximity of the conductive channel 26 from consumption of a secondary substrate 34 in a fluid that is exposed to the pH sensor 20. In the complex 30C, the ratio of the polymerase 28 to the metal coordination complex M is 1:1. The metal coordination complex M may be attached to directly to a polymerase 28, or a tether may link the two together.

The polymerase 28 of the complex 30C may be any example of the polymerase described in reference to FIG. 2.

The metal coordination complex 50E is similar to the enzyme 50A, in that it generates an acid or base in a reaction with the secondary substrate 34. Examples of the metal coordination complex include copper (II) complexes with ligands such as bis(2-pyridylmethyl)-amine or pyridine functionalized cyclodextrin.

In the complex 30C, the polymerase 28 and the metal coordination complex 50E are conjugated together. The complex 30C may be formed using any number of conjugation methods, such as a spytag-spycatcher coupling reaction, a π-clamp mediated cysteine conjugation, biotin/streptavidin, a SUMO (small ubiquitin-like modifier) protein, His6/NTA chelation with the metal, cysteine/maleimide, dibenzocyclooctyne (DBCO)/azide, or any other suitable conjugation method.

The complex 30C may be attached to the conductive channel 26. In the example shown in FIG. 5, the metal coordination complex 50E is attached to the surface of the channel 26, and the polymerase 28 is attached to the metal coordination complex 50E. In this example, the attachment of the complex 30C may be through a tether 32 (not shown in FIG. 5) or a terminal group of the metal coordination complex 50E. In another example, the polymerase 28 is attached to the surface of the channel 26, and the metal coordination complex 50E is attached to the polymerase 28. In this example, the attachment of the complex 30C may be through a tether 32 (not shown in FIG. 5) attached to the polymerase 28.

While not shown, the sensing system 10D may also include a detector to detect voltage and/or current changes that correspond with the pH change taking place at or near the surface of the pH sensing channel 26.

Also while not shown, the sensing system 10D may be positioned on a support, such as a silicon chip. The electrodes 22, 24 may be connected to electronic circuitry that enables their operation (e.g., once hooked up to a detector and power supply).

In some examples, the sensor 10D may come pre-assembled.

In other examples, the sensor components may be part of a kit, and the kit components may be used to assemble the sensor 10D. An example of the kit includes the pH sensor 20 on the support, and a fluid that is used to introduce the complex 30C to the pH sensor 20. The fluid includes a liquid carrier and the complex 30C. In an example, the liquid carrier is water or an example of the low buffer fluid, such as saline citrate at milli-molar concentrations.

When using these examples of the kit, a user can deposit the fluid on the support, and allow the fluid to remain on the support for a suitable time for the tether 32 or the terminal end of the metal coordination complex 50E to attach the complex 30C to the conductive channel 26. The support may be rinsed with a suitable buffer to remove any non-bound complexes 30C.

Some examples of the kit may also include fluid(s) that is/are to be used with the sensing system 10D during single molecule sensing. In this example, the fluid(s) included any example of the liquid carrier disclosed herein, the labeled nucleotides 12 or 12A-12C, and the secondary substrate 34 (which, in these examples, is a separate molecule from the labeled nucleotides 12 or 12A-12C).

The label 18E that is attached to the labeled nucleotides 12 or 12A-12C may be a ligand for a metal of the metal coordination complex 50E, wherein the ligand alters a catalytic property of the metal coordination complex 50E. The ligand may be selected to enhance the kinetics of the metal coordination complex 50E, or slow the kinetics of the metal coordination complex 50E. In these examples, the label 18E is one example of a pH altering moiety that is attached to the labeled nucleotide 12 or 12A-12C. This example of the system 10D thus includes two different examples of the pH altering moiety (e.g., the metal coordination complex 50E and the label 18E).

Other examples of the label 18E may function as a separate catalyst (in addition to the metal coordination complex 50E) for the consumption of the secondary substrate 34. Examples of labels 18E that function as separate catalysts include non-metal organocatalysts, such as diazabicycloundecene, N-heterocyclic carbenes, tetramethylguanidine, etc. In these examples, the label 18E is one example of a pH altering moiety that is attached to the labeled nucleotide 12 or 12A-12C. This example of the system 10D thus includes two different examples of the pH altering moiety (e.g., the metal coordination complex 50E and the label 18E).

Still other examples of the label 18E slow the kinetics of the metal coordination complex 50E, and thus also slow the kinetics of the acid or base generating reaction involving the metal coordination complex 50E and the secondary substrate 34. Examples of labels 18E that slow the kinetics of the metal coordination complex 50E may be any ligand that inhibits the catalytic activity of the metal, or any ligand that alters the electronic state of the metal to change the catalytic activity of the metal. In these examples, the label 18E is one example of a pH altering moiety that is attached to the labeled nucleotide 12 or 12A-12C. This example of the system 10D thus includes two different examples of the pH altering moiety (e.g., the metal coordination complex 50E and the label 18E).

In an example, the respective labels 18E that are attached to different nucleotides 12 or 12A-12C (e.g., A, T, C, G) may be selected to increase or decrease acid or base generation at different rates. In this example, when one of the labeled nucleotide 12 or 12A-12C is being incorporated by the polymerase 28, the label 18E is brought within proximity of the metal coordination complex 50E and the secondary substrate 34, and enhances or slows the reaction at a unique, label-dependent rate. In turn, the pH at the conductive channel 26 is altered. The change in pH correlates with increased or decreased acid or base generation, and thus can be used to identify the incorporated labeled nucleotide 12 or 12A-12C.

Because the labeled nucleotides 12 or 12A-12C do not include the secondary substrate 34, the fluid(s) represented in the example of FIG. 5 also include the secondary substrate 34. The secondary substrate 34 may be any secondary substrate 34 that can react with the metal coordination complex 50E to generate an acid or base.

The following description relates to an example method that involves the labeled nucleotides 12 and the sensing system 10D. In this example, the template polynucleotide chain 44 may be introduced to the sensing system 10D in a fluid, such as a biologically stable solution, together with or separate from the labeled nucleotides 12 and the secondary substrate 34. The polymerase 28 associates with the template polynucleotide chain 44, so that the chain 44 is held in place. A complementary base of one of the labeled nucleotides 12 will be incorporated into a nascent strand 46 (that is being formed along the template polynucleotide chain 44) by the polymerase 28. During the incorporation event, the label 18E of the labeled nucleotide 12 is brought into proximity of the channel 26, the metal coordination complex 50E, and any secondary substrate 34 in the fluid that is also within proximity of the metal coordination complex 50E. In some examples, the acid or base generating reaction with the secondary substrate 34 may be enhanced, slowed down, or inhibited depending upon the ligand label 18E and its effect on the reaction involving the metal coordination complex 50E. In other examples, the label 18E may participate in the consumption of the secondary substrate 34 along with the metal coordination complex 50E, thus generating more acid or base. All of these examples alter the pH of the fluid, and the charge, at the channel 26 surface. In these example methods, after incorporation of the nucleotide base into the nascent strand 46, the bond between the alpha phosphate and the linking molecule 16 or between the alpha phosphate and beta phosphate is naturally cleaved. In these examples, it may be desirable for the bonding of the ligand label 18E to be weak enough to fall off when the phosphate chain is naturally cleaved. This natural cleavage enables the label 18E (and the linking molecule 16) to dissociate from the incorporated nucleotide base and diffuse away from the sensing system 10D. The polymerase 28 can then receive another labeled nucleotide 12 which includes a nucleotide base that is complementary to the next nucleotide in the template polynucleotide chain 44.

The following description relates to an example method that involves the labeled nucleotides 12A-12C and the sensing system 10D. In this example, the template polynucleotide chain 44 may be introduced to the sensing system 10D in a fluid, such as a biologically stable solution, together with or separate from the labeled nucleotides 12A-12C and the secondary substrate 34. The polymerase 28 associates with the template polynucleotide chain 44, so that the chain 44 is held in place. A complementary base of one of the labeled nucleotides 12A-12C will be incorporated into a nascent strand 46 (that is being formed along the template polynucleotide chain 44) by the polymerase 28. In some examples, the acid or base generating reaction with the secondary substrate 34 may be enhanced, slowed down, or inhibited depending upon the ligand label 18E and its effect on the reaction involving the metal coordination complex 50E. In other examples, the label 18E may participate in the consumption of the secondary substrate 34 along with the metal coordination complex 50E, thus generating more acid or base. All of these examples alter the pH of the fluid, and the charge, at the channel 26 surface. In this example, the labeled nucleotide 12A-12C includes a reversible terminator. As such, incorporation of the labeled nucleotide 12A-12C serves as a terminator for polymerization. This enables the enhanced, slowed down, or inhibited acid or base generation and charge detection to take place in a similar manner as described above. In this example method, washing and exposure to a de-blocking agent may be used to prepare the sensing system 10D for another sequencing cycle.

In any of the examples described in reference to FIG. 5, it is to be understood that the distance between the polymerase 28 and the metal coordination complex 50E and the length of the linking molecule 16, 16' may be selected so that the label 18E is brought within proximity of the metal coordination complex 50E when its labeled nucleotide 12 or 12A-12C is being incorporated by the polymerase 28. This enables predictable effects on the acid or base generating reaction.

Sensing System 10E

Figure 6A:
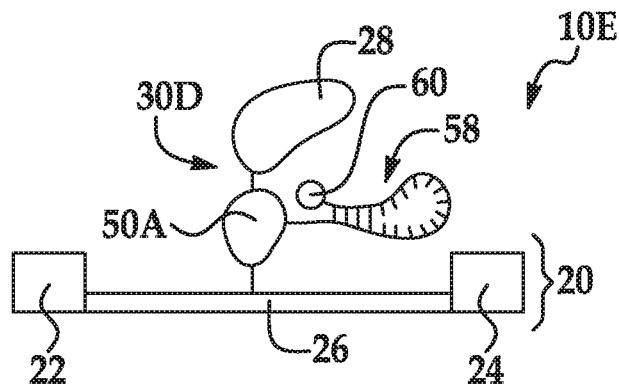
FIG. 6A is a schematic illustration depicting yet another example of the sensing system disclosed herein.
Figure 6B:
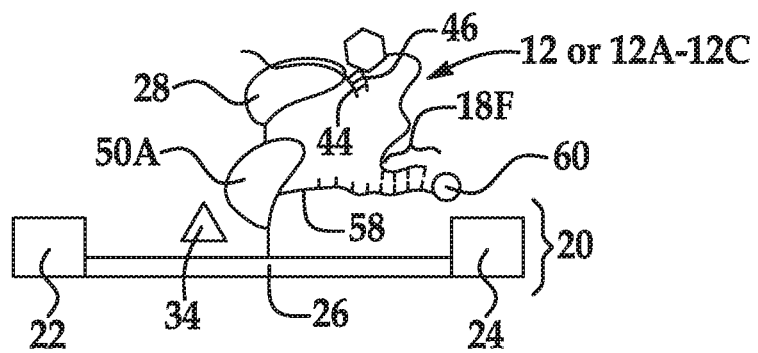
FIG. 6B depicts the example of the sensing system of FIG. 6A in use with another example of the labeled nucleotide disclosed herein.

Referring specifically to FIG. 6A and FIG. 6B, the sensing system 10D includes the pH sensor 20 and a complex 30D attached to the conductive channel 26 of the pH sensor 20.

The complex 30D includes the polymerase 28 linked to an enzyme 50A. In this example, the complex 30D further includes a nucleic acid hairpin-enzyme inhibitor conjugate 58 attached to the enzyme 50A.

The polymerase 28 of the complex 30D may be any examples of the polymerase described in reference to FIG. 2.

The enzyme 50A may be any example of the enzyme described in reference to FIG. 3A and FIG. 3B.

The nucleic acid hairpin-enzyme inhibitor conjugate 58 includes a single stranded DNA or RNA having two regions that are complementary and that undergo intramolecular base-pairing to form a double helix that ends in an unpaired loop. One end of the unpaired loop is attached to the enzyme 50A, and the other end of the unpaired loop includes an enzyme inhibitor 60. When in the looped configuration as shown in FIG. 6A, the enzyme inhibitor 60 at least reduces enzyme activity.

In the complex 30D, the enzyme 50A and the nucleic acid hairpin-enzyme inhibitor conjugate 58 are conjugated together, and the enzyme 50A is also conjugated to the polymerase 28.

The complex 30D may be attached to the conductive channel 26 through a tether 32, examples of which are described in reference to FIG. 2. Alternatively, the complex 30D may be directly attached via bonding between the pH altering moiety 50A and groups at the surface of the conductive channel 26.

While not shown, the sensing system 10E may also include a detector to detect voltage and/or current changes that correspond with the pH change taking place at or near the surface of the pH sensing channel 26.

Also while not shown, the sensing system 10E may be positioned on a support, such as a silicon chip. The electrodes 22, 24 may be connected to electronic circuitry that enables their operation (e.g., once hooked up to a detector and power supply).

In some examples, the sensor 10E may come pre-assembled.

In other examples, the sensor components may be part of a kit, and the kit components may be used to assemble the sensor 10E. An example of the kit includes the pH sensor 20 on the support, and a fluid that is used to introduce the complex 30D to the pH sensor 20. The fluid includes a liquid carrier and the complex 30D. In some examples, the complex 30D in the fluid is attached to the tether 32. In other examples, the tether 32 is attached to the pH sensing channel 26 as part of the sensing system 10E. In still other examples where there is a direct bond formed between the pH altering moiety 50A and the surface groups of the channel 26, it is to be understood that the complex 30D in the fluid is not attached to the tether 32 and the tether 32 is not attached to the pH sensing channel 26. In an example, the liquid carrier is water or an example of the low buffer fluid, such as saline citrate at milli-molar concentrations.

When using these examples of the kit, a user can deposit the fluid on the support, and allow the fluid to remain on the support for a suitable time for the tether 32 to attach the complex 30D to the conductive channel 26, for the complex 30D to attach to a tether 32 on the channel 26, or for the pH altering moiety 50A to bond to the surface groups of the channel 26. The support may be rinsed with a suitable buffer to remove any non-bound complexes 30D.

Some examples of the kit may also include fluid(s) that is/are to be used with the sensing system 10E during single molecule sensing. In this example, the fluid(s) included any example of the liquid carrier disclosed herein, the labeled nucleotides 12 or 12A-12C, and the secondary substrate 34 (which, in these examples, is a separate molecule from the labeled nucleotides 12 or 12A-12C).

The label 18F that is attached to the labeled nucleotides 12 or 12A-12C is a strand of nucleotides including bases complementary to at least some of the nucleotide bases of the nucleic acid hairpin-enzyme inhibitor conjugate 58. The label 18F is capable of initiating a hairpin opening reaction and then base-pairing with a portion of the single DNA or RNA strand of the nucleic acid hairpin-enzyme inhibitor conjugate 58. As shown in FIG. 6B, the introduction and reaction of the label 18F moves the enzyme inhibitor 60 away from the enzyme 50A, thus enabling its enzymatic activity. Because the label 18F may affect the enzymatic activity that leads to acid or base generation, it is also one example of a pH altering moiety. The acid or base generating reaction with the secondary substrate 34 is able to take place when the label 18F opens up the nucleic acid hairpin-enzyme inhibitor conjugate 58, resulting in the change in pH at the surface of the conductive channel 26. The opening and closing of the hairpin may be a rapid process, resulting in an averaged level of inhibition of the polymerase 28. Thus, different levels of activity or inhibition can be achieved using different number of complementary bases, thus enabling base discrimination.

Because the labeled nucleotides 12 or 12A-12C do not include the secondary substrate 34, the fluid(s) represented in the example of FIGS. 6A and 6B also include the secondary substrate 34. The secondary substrate 34 may be any secondary substrate 34 that can react with the enzyme 50A to generate an acid or base.

The following description relates to an example method that involves the labeled nucleotides 12 and the sensing system 10E. In this example, the template polynucleotide chain 44 may be introduced to the sensing system 10E in a fluid, such as a biologically stable solution, together with or separate from the labeled nucleotides 12 and the secondary substrate 34. The polymerase 28 associates with the template polynucleotide chain 44, so that the chain 44 is held in place. A complementary base of one of the labeled nucleotides 12 will be incorporated into a nascent strand 46 (that is being formed along the template polynucleotide chain 44) by the polymerase 28. During the incorporation event, the label 18F of the labeled nucleotide 12 is brought into proximity of the channel 26, the nucleic acid hairpin-enzyme inhibitor conjugate 58, and any secondary substrate 34 in the fluid that is also within proximity of the nucleic acid hairpin-enzyme inhibitor conjugate 58. The label 18F opens the nucleic acid hairpin-enzyme inhibitor conjugate 58, which allows the enzyme 50A to react with the secondary substrate 34 to generate an acid or a base. This alters the pH of the fluid, and the charge, at the channel 26 surface. In this example method, after incorporation of the nucleotide base into the nascent strand 46, the bond between the alpha phosphate and the linking molecule 16 or between the alpha phosphate and beta phosphate is naturally cleaved. In these examples, it may be desirable for the bonding of the ligand label 18F to be weak enough to fall off when the phosphate chain is naturally cleaved. This natural cleavage enables the label 18F (and the linking molecule 16) to dissociate from the incorporated nucleotide base and diffuse away from the sensing system 10E. The nucleic acid hairpin-enzyme inhibitor conjugate 58 revert to the stem loop position, thereby again at least partially inhibiting the enzyme 50A activity. The polymerase 28 can then receive another labeled nucleotide 12 which includes a nucleotide base that is complementary to the next nucleotide in the template polynucleotide chain 44.

The following description relates to an example method that involves the labeled nucleotides 12A-12C and the sensing system 10E. In this example, the template polynucleotide chain 44 may be introduced to the sensing system 10C in a fluid, such as a biologically stable solution, together with or separate from the labeled nucleotides 12A-12C and the secondary substrate 34. The polymerase 28 associates with the template polynucleotide chain 44, so that the chain 44 is held in place. A complementary base of one of the labeled nucleotides 12A-12C will be incorporated into a nascent strand 46 (that is being formed along the template polynucleotide chain 44) by the polymerase 28. The label 18F opens the nucleic acid hairpin-enzyme inhibitor conjugate 58, which allows the enzyme 50A to react with the secondary substrate 34 to generate an acid or a base. This alters the pH of the fluid, and the charge, at the channel 26 surface. In this example, the labeled nucleotide 12A-12C includes a reversible terminator. As such, incorporation of the labeled nucleotide 12A-12C serves as a terminator for polymerization. This enables the acid or base generation and charge detection to take place in a similar manner as described above. In this example method, washing and exposure to a de-blocking agent may be used to prepare the sensing system 10E for another sequencing cycle.

In any of the examples described in reference to FIGS. 6A and 6B, it is to be understood that the distance between the polymerase 28 and the nucleic acid hairpin-enzyme inhibitor conjugate 58, and the length of the linking molecule 16, 16' may be selected so that the label 18F is brought within proximity of the nucleic acid hairpin-enzyme inhibitor conjugate 58 when its labeled nucleotide 12 or 12A-12C is being incorporated by the polymerase 28. This enables predictable effects on the acid or base generating reaction.

Sensing System Arrays

Any example of the single molecule sensing systems 10A-10E may be included in an array of such sensing systems. In some examples, an array may include several sensing systems 10A-10E, each of which is positioned on a support and is configured with electronic circuitry so that it is individually addressable and readable. In an example, each sensing system 10A-10E of the array may be positioned on the support in an individual depression. The depressions physically separate each of the sensing systems 10A-10E, which at least reduces cross-contamination of the pH gradients to adjacent sensing systems 10A-10E. The array of sensing systems 10A-10E may be part of a flow cell 62, an example of which is depicted in FIG. 7A. In this example, the flow cell 62 includes flow channels 64. While several flow channels 64 are shown, it is to be understood that any number of channels 64 may be included in the flow cell 62 (e.g., a single channel 64, four channels 64, etc.). Each flow channel 64 is an area defined between two bonded components (e.g., a substrate and a lid, or two substrates), which can have fluids (e.g., those describe herein) introduced thereto and removed therefrom. Each flow channel 64 may be isolated from each other flow channel 64 so that fluid introduced into any particular flow channel 64 does not flow into any adjacent flow channel 64. Some examples of the fluids introduced into the flow channels 64 may introduce reaction components (e.g., complexes 30A-30D, labeled nucleotides 12, 12A-12C, 12', etc.), washing solutions, deblocking agents, etc.

Figure 7B:
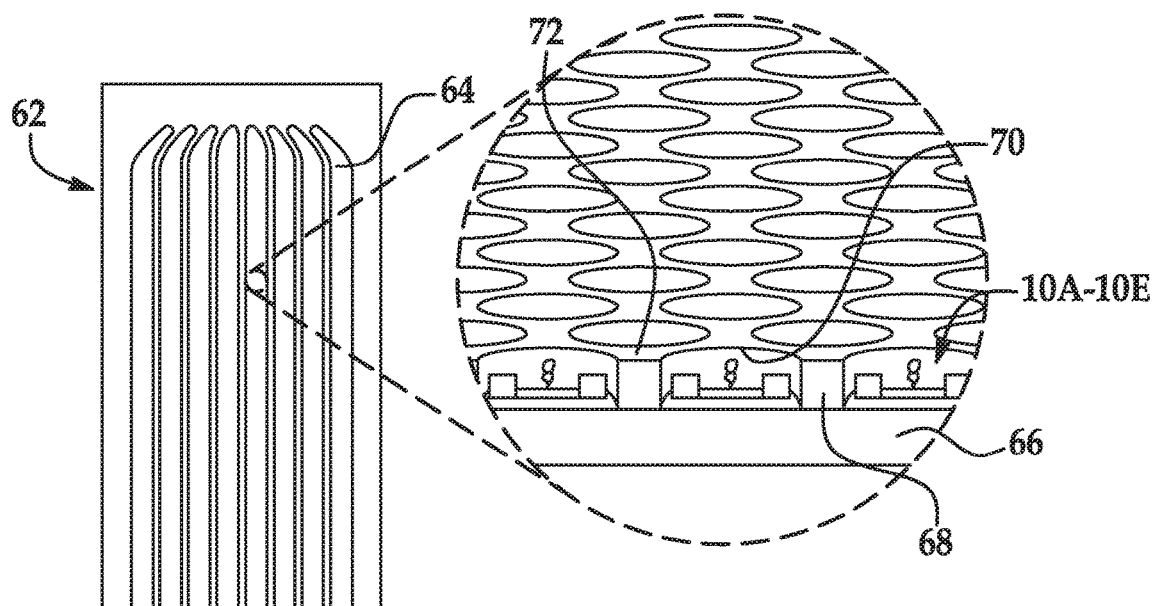
FIG. 7B is an enlarged, and partially cutaway view of an example of a flow cell suitable for use with single molecule sensing.
Figure 7C:
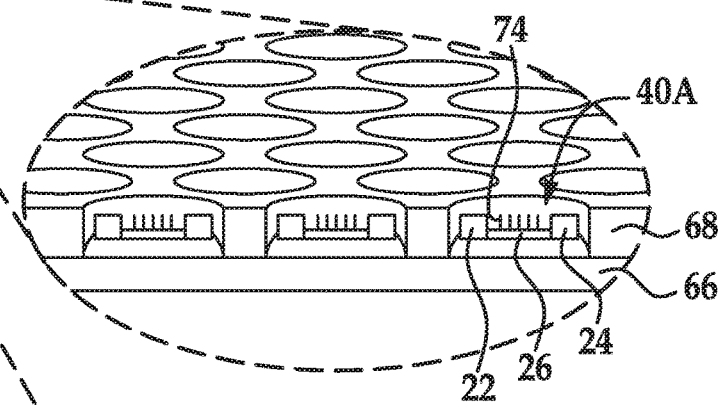
FIG. 7C is an enlarged, and partially cutaway view of an example of a flow cell suitable for use with ensemble sequencing.
Figure 7D:
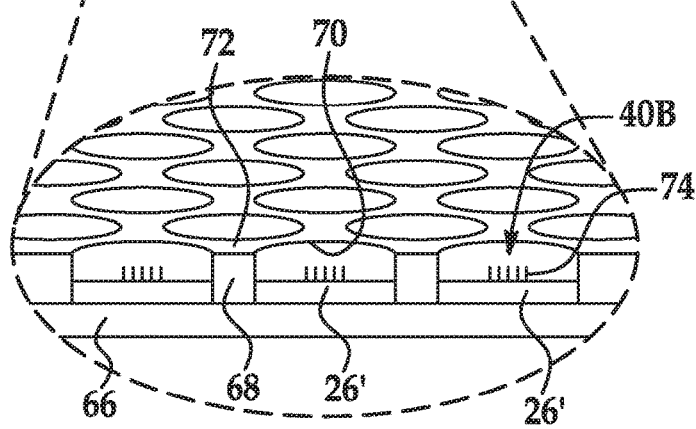
FIG. 7D is an enlarged, and partially cutaway view of still another example of a flow cell suitable for use with ensemble sequencing.

An example of the architecture within the flow channels 64 of the flow cell 62 is shown FIG. 7B.

In the example shown in FIG. 7B, the flow cell 64 includes a support 66 and a patterned material 68 positioned on the support 66. The patterned material 68 defines depressions 70 separated by interstitial regions 72. In this example, a surface of the support 66 is exposed at each of the depressions 70, and a sensing system 10A-10E is positioned on the surface.

The support 66 in FIG. 7B provides support for the other components of the flow cell 62. The support 66 is generally rigid and is insoluble in an aqueous liquid. Examples of suitable supports 66 include epoxy siloxane, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HfO_2$), inorganic glasses, or the like. Some examples of suitable plastics for the substrate 14 include acrylics, polystyrene, copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc. The support may also be glass or silicon, with a coating layer of tantalum oxide or another ceramic oxide at the surface.

The form of the support 66 may be a wafer, a panel, a rectangular sheet, a die, or any other suitable configuration. In an example, the support 66 may be a circular wafer or panel having a diameter ranging from about 2 mm to about 300 mm. As a more specific example, the support 66 is a wafer having a diameter ranging from about 200 mm to about 300 mm. In another example, the support 66 may be a rectangular sheet or panel having its largest dimension up to about 10 feet (~3 meters). As a specific example, the support 66 is a die having a width ranging from about 0.1 mm to about 10 mm. While example dimensions have been provided, it is to be understood that a support 66 with any suitable dimensions may be used.

In the example shown in FIG. 7B, the patterned material 68 is positioned on the support 66. It is to be understood that any material that can be selectively deposited, or deposited and patterned to form the depressions 70 and the interstitial regions 72 may be used for the patterned material 68.

As one example, an inorganic oxide may be selectively applied to the support 66 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example, a resin may be applied to the support 66 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (POSS) refers to a chemical composition that is a hybrid intermediate (e.g., $RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units.

As still another example, the patterned material 68 may be a pH buffer material. A pH buffer material has a high pH buffering capacity, which enables the use of a fluid with low solution buffer concentration. An example of a high pH buffering capacity may range from about 0.01 meq/g to about 2 meq/g. An example of a pH buffer material is SiCOH, which has a high surface area and a high buffering capacity. In examples where the patterned material 68 is not a pH buffer material, the sidewalls of the depressions 70 may be coated with the pH buffer material to impart the high pH buffering capacity to each of the depressions 70.

As shown in FIG. 7B, the patterned material 68 includes the depressions 70 defined therein, and interstitial regions 72 separating adjacent depressions 70. Many different layouts of the depressions 70 may be envisaged, including regular, repeating, and non-regular patterns. In an example, the depressions 70 are disposed in a hexagonal grid for close packing and improved density. Other layouts may include, for example, rectilinear (rectangular) layouts, triangular layouts, and so forth. In some examples, the layout or pattern can be an x-y format of depressions 70 that are in rows and columns. In some other examples, the layout or pattern can be a repeating arrangement of depressions 70 and/or interstitial regions 72. In still other examples, the layout or pattern can be a random arrangement of depressions 70 and/or interstitial regions 72. The pattern may include spots, pads, wells, posts, stripes, swirls, lines, triangles, rectangles, circles, arcs, checks, plaids, diagonals, arrows, squares, and/or cross-hatches.

The layout or pattern of the depressions 70 may be characterized with respect to the density of the depressions 70 (number of depressions 70) in a defined area. For example, the depressions 70 may be present at a density of approximately 2 million per mm$^2$. The density may be tuned to different densities including, for example, a density of about 100 per mm$^2$, about 1,000 per mm$^2$, about 0.1 million per mm$^2$, about 1 million per mm$^2$, about 2 million per mm$^2$, about 5 million per mm$^2$, about 10 million per mm$^2$, about 50 million per mm$^2$, or more, or less. It is to be further understood that the density of depressions 70 in the patterned material 68 can be between one of the lower values and one of the upper values selected from the ranges above. As examples, a high density array may be characterized as having depressions 70 separated by less than about 100 nm, a medium density array may be characterized as having depressions 20 separated by about 400 nm to about 1 µm, and a low density array may be characterized as having depressions 70 separated by greater than about 1 µm. While example densities have been provided, it is to be understood any suitable densities may be used. The density of the depressions 70 may depend, in part, on the depth of the depressions 70 and the diffusion capability of the generated acid or base. In some instances, it may be desirable for the spacing between depressions to be even greater than the examples listed herein.

The layout or pattern of the depressions 70 may also or alternatively be characterized in terms of the average pitch, or the spacing from the center of the depression 70 to the center of an adjacent depression 70 (center-to-center spacing) or from the edge of one depression 70 to the edge of an adjacent depression 70 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 20 can be between one of the lower values and one of the upper values selected from the ranges above. In an example, the depressions 20 have a pitch (center-to-center spacing) of about 1.5 µm. While example average pitch values have been provided, it is to be understood that other average pitch values may be used.

The size of each depression 70 may be characterized by its volume, opening area, depth, and/or diameter.

Each depression 70 can have any volume that is capable of confining a fluid. The minimum or maximum volume can be selected, for example, to accommodate the throughput (e.g., multiplexity), resolution, labeled nucleotides 12, 12A-12C or 12', secondary substrates 34, or analyte reactivity expected for downstream uses of the flow cell 62. For example, the volume can be at least about $1\times10^{-3}$ µm$^3$, at least about $1\times10^{-2}$ µm$^3$, at least about 0.1 µm$^3$, at least about 1 µm$^3$, at least about 10 µm$^3$, at least about 100 µm$^3$, or more. Alternatively or additionally, the volume can be at most about $1\times10^4$ µm$^3$, at most about $1\times10^3$ µm$^3$, at most about 100 µm$^3$, at most about 10 µm$^3$, at most about 1 µm$^3$, at most about 0.1 µm$^3$, or less. The area occupied by each depression opening can be selected based upon similar criteria as those set forth above for the volume. For example, the area for each depression opening can be at least about $1\times10^{-3}$ µm$^2$, at least about $1\times10^{-2}$ µm$^2$, at least about 0.1 µm$^2$, at least about 1 µm$^2$, at least about 10 µm$^2$, at least about 100 µm$^2$, or more. Alternatively or additionally, the area can be at most about $1\times10^3$ µm$^2$, at most about 100 µm$^2$, at most about 10 µm$^2$, at most about 1 µm$^2$, at most about 0.1 µm$^2$, at most about $1\times10^{-2}$ µm$^2$, or less. The area occupied by each depression opening can be greater than, less than or between the values specified above.

The depth of each depression 70 can be large enough to house one sensing system 10A-10E. In an example, the depth may be at least about 1 µm, at least about 10 µm, at least about 100 µm, or more. Alternatively or additionally, the depth can be at most about $1\times10^3$ µm, at most about 100 µm, at most about 10 µm, or less. The depth of each depression 70 can be greater than, less than or between the values specified above.

In some instances, the diameter or length and width of each depression 70 can be at least about 50 nm, at least about 0.1 µm, at least about 0.5 µm, at least about 1 µm, at least about 10 µm, at least about 100 µm, or more. Alternatively or additionally, the diameter or length and width can be at most about $1\times10^3$ µm, at most about 100 µm, at most about 10 µm, at most about 1 µm, at most about 0.5 µm, at most about 0.1 µm, or less (e.g., about 50 nm). The diameter or length and width of each depression 70 can be greater than, less than or between the values specified above.

As depicted in FIG. 7B, each of the depressions 70 in the array includes a respective sensor 10A-10E. It is desirable for each sensor 10A-10E in each depression 70 to have one polymerase 28, alone or as part of a complex 30A-30D, attached thereto. In some examples, each sensor 10A-10E in each depression 70 has one polymerase 28 or complex 30A-30D attached thereto. In other examples, some sensors 10A-10E in some depressions 70 have one polymerase 28 or complex 30A-30D attached thereto; other sensors 10A-10E in other depressions 70 have more than one polymerase 28 or complex 30A-30D attached thereto; and still other sensors 10A-10E in other depressions 70 have no polymerase 28 or complex 30A-30D attached thereto. In these examples, the number of polymerase(s) 28 or complex(es) 30A-30D that become attached to any given sensing system 10A-10E may be random and determined by the Poisson distribution.

To attach the polymerases 28 or complexes 30A-30D, the method includes introducing a fluid to a sensor array including a plurality of individually addressable conductive channels 26, thereby attaching a polymerase 28 or a complex 30A-30D to at least some of the plurality of individually addressable conductive channels 26, the complex 30A-30D including a polymerase 28 and different examples of the pH altering moiety 50A-50E linked to the polymerase 28, the pH altering moiety 50A-50E being selected from the group consisting of an enzyme 50A that is to catalyze consumption of a secondary substrate 34 in a solution that is to be exposed to the sensor array, a metal coordination complex 50E that is to catalyze consumption of the secondary substrate 34 in the solution that is to be exposed to the sensor array, and a co-factor 50B or an activator 50C of a catalyst label attached to a labeled nucleotide that is to be introduced to the sensor array. The fluid may be allowed to incubate for a desirable time and at a desirable temperature to allow the polymerases 28 or the complexes 30A-30D to attach.

During any examples of the methods disclosed herein for single molecule sensing, one of the labeled nucleotides 12 or 12A-12C or 12' is incorporated, by a respective polymerase 28, into a nascent strand 46 that is being formed at the sensing system 10A-10E in each of the depressions 70. In other words, at each template polynucleotide chain 44 across the flow cell 62, respective polymerases 28 extend the nascent strand 46 by one of the nucleotides 12, 12A-12C, or 12' present in the introduced fluid.

Each of the sensors 10A-10E is individually electrically addressable and readable. As such, the charge signals resulting from pH changes taking place within each depression 70, in response to the consumption of the secondary substrate 34, may be individually detected and analyzed to identify the incorporated labeled nucleotide 12, 12A-12C, or 12'. The acid or base generating reaction taking place within each depression will depend on the label 18A-18F and the polymerase 28 or complex 30A-30D combination that is used, examples of which are described in reference to FIG. 3A and FIG. 3B, FIG. 4, FIG. 5, and FIG. 6A and FIG. 6B.

Ensemble Detection

Other examples of the sensing systems 40A and 40B are shown in FIG. 7C and FIG. 7D, and these sensing systems 40A and 40B may be used in ensemble sensing. In these examples, the sensing systems 40A and 40B may be positioned in each of the depressions 70 of the flow cell 62. The flow cell 62 includes the channels 64, support 66, patterned material 68, and the patterned material 68 as described herein.

In the example shown in FIG. 7C, the sensing system 40A includes the pH sensor 20 and primers 74 attached to the conductive channel 26 of the pH sensor 20 and/or to the surface of the support 66 exposed at each depression 70.

The surface of the support 66 exposed at the depressions 70 may be functionalized so that primers 74 can attach to the surface and not to the interstitial regions 72 of the patterned material 68. In some examples, functionalizing the support surface involves silanizing the surface exposed at the depressions 70 and forming a polymer layer on the silanized surface. Silanization may be accomplished using any silane or silane derivative. A polymer (not shown) may then be applied to the silanized surface. The polymer may be a semi-rigid polymeric material that is permeable to liquids and gases. An example of the polymer includes an acrylamide copolymer, such as poly(N-(5-azidoacetamidylpentyl)acrylamide-co-acrylamide, PAZAM, or another suitable polymeric hydrogel.

The primers 74 may be any forward amplification primer or reverse amplification primer that includes a functional group that can attach to the surface of the conductive channel 26 and/or to the surface of the support 66. Examples of suitable functional group terminated primers include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer. A mixture of primers may also be used. Specific examples of suitable primers include P5 and/or P7 primers, which are used on the surface of some commercial flow cells sold by Illumina Inc.

In an example, the primers 74 may be attached using a grafting process, such as flow through deposition (e.g., when the flow cell 62 has a lid bonded thereto), dunk coating, spray coating, puddle dispensing, or by another suitable method that will attach the primer(s) 74. Each of these example techniques may utilize a primer solution or mixture, which may include the primer(s), water, a buffer (e.g., a salt solution), and a catalyst.

In the example shown in FIG. 7D, the sensing system 40B includes a planar conductive channel 26' and primers 74 attached to the planar conductive channel 26'. The planar conductive channel 26' may be any material that is capable of sensing charged ions, or that includes surface groups that can be protonated or deprotonated by charged ions generated during the acid or base generating reactions disclosed herein.

The planar conductive channel 26' is connected to electrodes 22, 24 (not shown in FIG. 7D) that may be integrated into the support 66 and connected to electronic circuitry that enables their operation. Any of the primers 74 may be used and may be attached as described herein. Moreover, if the planar conductive channel 26' has surface groups that can attach the primers 74, additional functionalization of the planar conductive channel 26' may not be performed.

These examples of the flow cell 62 may be used for ensemble sequencing. In ensemble sequencing, a template polynucleotide chain 44 (not shown in FIG. 7C and FIG. 7D) that is to be sequenced may be formed on the flow cell surface using the primers 74. At the outset of template polynucleotide chain formation, library templates may be prepared from any nucleic acid sample (e.g., a DNA sample or an RNA sample). The nucleic acid sample may be fragmented into single-stranded, similarly sized (e.g., <1000 bp) DNA or RNA fragments. During preparation, adapters may be added to the ends of these fragments. Through reduced cycle amplification, different motifs may be introduced in the adapters, such as sequencing binding sites, indices, and regions that are complementary to the primers 74 in the depressions 70. The final library templates include the DNA or RNA fragment and adapters at both ends. In some examples, the fragments from a single nucleic acid sample have the same adapters added thereto.

A plurality of library templates may be introduced to the flow cell 62. Because the flow cell 62 includes an array of depressions 70, multiple library templates are hybridized, for example, to one of two types of primers 74 immobilized therein.

Cluster generation may then be performed. In one example of cluster generation, the library templates are copied from the hybridized primers 74 by 3' extension using a high-fidelity DNA polymerase. The original library templates are denatured, leaving the copies immobilized in the depressions 70. Isothermal bridge amplification may be used to amplify the immobilized copies. For example, the copied templates loop over to hybridize to an adjacent, complementary primer 74, and a polymerase copies the copied templates to form double stranded bridges, which are denatured to form two single stranded strands. These two strands loop over and hybridize to adjacent, complementary primers 74 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide chains 44 in each depression 70. This example of clustering is bridge amplification, and is one example of the amplification that may be performed. It is to be understood that other amplification techniques may be used, such as the exclusion amplification (Examp) workflow (Illumina Inc.).

To initiate sequencing, an incorporation mix may be added to the flow cell 62.

In one example, the incorporation mix includes a liquid carrier, any example of the complex 30A-30D disclosed herein, and any example of the labeled nucleotide 12 or 12A-12C. The complex 30A-30D includes a polymerase 28 and a pH altering moiety 50A-50E linked to the polymerase 28, the pH altering moiety 50A-50E being selected from the group consisting of an enzyme 50A that is to catalyze consumption of a secondary substrate 34, a metal coordination complex 50D that is to catalyze consumption of the secondary substrate 34, and a co-factor 50B or an activator 50C that is to catalyze consumption of the secondary substrate 34. The labeled nucleotide 12 includes a nucleotide 14; a linking molecule 16 attached to a terminal phosphate group of the nucleotide 14; and a label 18 attached to the linking molecule 16, wherein the label is to participate in a pH altering reaction involving the secondary substrate 34. The labeled nucleotide 12A-12C includes a nucleotide 14' having a 3' OH blocking group; a cleavable linking molecule 16' attached to a base or a sugar of the nucleotide 14'; and a label 18 attached to the linking molecule 16', wherein the label 18 is to participate in a pH altering reaction involving the secondary substrate 34.

The label 18 of the labeled nucleotide 12 or 12A-12C will depend on the complex 30A-30D that is used, and the combinations and associated acid or base generating reactions as described in reference to FIG. 3A and FIG. 3B, FIG. 4, FIG. 5, and FIG. 6A and FIG. 6B may be used. As one example, when the pH altering moiety of the complex 30A is the enzyme 50A, the label 18B is used, and may be selected from the group consisting of a first group that enhances kinetics of the enzyme 50A and a second group that slows kinetics of the enzyme 50A. As another example, the pH altering moiety is the metal coordination complex 50E, and the label 18E may be used. As discussed herein in reference to FIG. 5, the label 18E is a ligand for a metal of the metal coordination complex 50E, wherein the ligand alters a catalytic property of the metal coordination complex 50E. As still another example, the pH altering moiety is the co-factor 50B or activator 50C, and the label 18C is a catalyst label that is activated by the co-factor 50B or activator 50C. As yet another example, the pH altering moiety is the enzyme 50A, and the complex 30D includes the nucleic acid hairpin-enzyme inhibitor conjugate 58. The label 18F is the oligonucleotide sequence that is complementary to a portion of the nucleic acid hairpin-enzyme inhibitor conjugate 58.

The incorporation mix introduces the complex 30A-30D and the labeled nucleotide 12 or 12A-12C to the flow cell 62. The incorporation mix may also include a sequencing primer that hybridizes to a complementary sequence on the template polynucleotide chain 44. This sequencing primer renders the template polynucleotide chain 44 ready for sequencing.

Another fluid may be used to introduce the secondary substrate 34 to the flow cell 62. The incorporation mix and the fluid including the secondary substrate 34 may be part of a kit. Either example of the flow cell 62 (shown in FIG. 7C and FIG. 7D) may be included in the kit.

When the incorporation mix includes the labeled nucleotide 12 (the label 18 of which is naturally cleaved after incorporation), it is to be understood that the incorporation mix and the fluid with the secondary substrate 34 may be introduced into the flow cell 62 simultaneously or one right after the other, so that the secondary substrate 34 is present in the flow cell 62 during the incorporation event. Because the label 18 is naturally cleaved after incorporation, it is desirable for the secondary substrate 34 to be present while the label 18 is held within proximity of the conductive channel 26 or 26'. In contrast, when the incorporation mix includes the labeled nucleotide 12A-12C (which includes the blocking group and thus its label 18 is not naturally cleaved), it is to be understood that the incorporation mix and the fluid with the secondary substrate 34 may be introduced into the flow cell 62 simultaneously or one right after the other, or the fluid with the secondary substrate 34 may be introduced after incorporation has taken place. Because the label 18 remains tethered until a deblocking agent is introduced, the secondary substrate 34 may be introduced at any time during or after the incorporation event.

When the incorporation mix and the fluid with the secondary substrate 34 are introduced into the flow cell 62, the fluids enter the depressions 70 (where the template polynucleotide chains 44 are present). One of the labeled nucleotides 12 or 12A-12C is incorporated, by a respective polymerase 28 of a respective complex 30A-30D, into a nascent strand 46 that extends the sequencing primer and that is complementary to the template polynucleotide chain 44. In other words, in at least some of the template polynucleotide chains 44 across the flow cell 62, respective polymerases 28 extend the hybridized sequencing primer by one of the labeled nucleotides 12 or 12A-12C in the solution.

In these examples, because the polymerase 28 is part of the complex 30A-30D including the pH altering moiety 50A-50E and because the polymerase 28 participates in nucleotide incorporation, the pH altering moiety 50A-50E is brought within proximity of the conductive channel 26 or 26' during the incorporation event. The label 18 of the incorporated nucleotide 12 or 12A-12C is also brought into proximity of the pH altering moiety 50A-50E and the conductive channel 26, 26'. This enables the pH altering moiety 50A-50E and label 18 to participate in the acid or base generating reaction with the secondary substrate 34 near the conductive channel 26, 26'. The various reactions and the effects of the specific moiety 50A-50E and the label 18 combinations are the same as described in reference to FIG. 3A and FIG. 3B, FIG. 4, FIG. 5, and FIG. 6A and FIG. 6B. The change in pH as a result of the acid or base generating reaction alters the charge at the conductive channel 26, 26', and the change in charge is detected. The change in the charge and/or the rate of the change in charge may be used to identify the incorporated nucleotides. Because multiple incorporation events are taking place on multiple primers 74 within a single depression, the charge signals may be strong and readily detectable at each individual conductive channel 26, 26'.

In examples of ensemble sequencing including the labeled nucleotide 12, the label 18 and linking molecule 16 naturally cleave after incorporation.

In examples of ensemble sequencing including the labeled nucleotide 12A-12C, the label 18 and the linking molecule 16' remain incorporated until a deblocking agent is added and washed through the flow cell 62.

In some examples of ensemble sequencing, the polymerase 28 of the complex 30A-30D may be highly processive, and may thus may not need to be introduced with each sequencing cycle. In other examples, a fresh polymerase 28 (e.g., as part of a complex 30A-30D) may be introduced with each sequencing cycle.

In another example of ensemble sequencing using the flow cell 62 as described in reference to FIG. 7C and FIG. 7D, the incorporation mix may not include an example of the complex 30A-30D, but rather may include the polymerase 28 on its own. This example is similar to the example described in FIG. 2, except that the polymerase 28 is present in the incorporation mix and is not tethered to the surface of the conductive channel 26, 26'. This example of the incorporation mix may include a carrier liquid, the polymerase 28, and the labeled nucleotides 12 or 12A-12C including the label 18A; which, as described in reference to FIG. 2, is a catalyst that initiates or accelerates an acid or base generating reaction involving the secondary substrate 34. A second fluid including a carrier liquid and the secondary substrate 34 may be used with this example of the incorporation mix.

When this example of the incorporation mix and the fluid with the secondary substrate 34 are introduced to the example of the flow cell 62 shown in FIG. 7B and FIG. 7C, the fluids enter the depressions 70 (where the template polynucleotide chains 44 are present). One of the labeled nucleotides 12 or 12A-12C is incorporated, by a respective polymerase 28, into a nascent strand 46 that extends the sequencing primer and that is complementary to the template polynucleotide chain 44. In other words, in at least some of the template polynucleotide chains 44 across the flow cell 62, respective polymerases 28 extend the hybridized sequencing primer by one of the labeled nucleotides 12 or 12A-12C in the solution.

In these examples, the catalyst label 18A of the incorporated nucleotide 12 or 12A-12C is brought into proximity of the conductive channel 26, 26'. This enables catalyst label 18A to participate in the acid or base generating reaction with the secondary substrate 34 near the conductive channel 26. 26'. The various reactions and the effects of the catalyst label 18A are the same as described in reference to FIG. 2. The change in pH as a result of the acid or base generating reaction alters the charge at the conductive channel 26, 26', and the change in charge is detected. The change in the charge and/or the rate of the change in charge may be used to identify the incorporated nucleotides. Because multiple incorporation events are taking place any multiple primers 74 within a single depression, the charge signals may be strong and readily detectable at each individual conductive channel 26, 26'.

CONCLUSION

While single molecule detection and ensemble detection have been described in detail, it is to be understood that the acid or base generating reactions disclosed herein may be utilized with other sequencing protocol, for genotyping, or in other chemical and/or biological applications It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if they were explicitly recited. For example, a range represented by from 1 nm to less than 1 μm, should be interpreted to include not only the explicitly recited limits of from 1 nm to less than 1 μm, but also to include individual values, such as about 5 nm, 222.5 nm, 275 nm, etc., and sub-ranges, such as from about 150 nm to about 800 nm, etc.

While several examples have been described in detail, it is to be understood that the disclosed examples may be modified. Therefore, the foregoing description is to be considered non-limiting.

What is claimed is:

1. A sensing system, comprising:
    a pH sensor, including:
       two electrodes; and
       a conductive channel operatively connected to the two electrodes; and
    a complex attached to the conductive channel of the pH sensor, the complex including a polymerase linked to at least one pH altering moiety that is to participate in generating a pH change within proximity of the conductive channel from consumption of a secondary substrate in a fluid that is exposed to the pH sensor, the at least one pH altering moiety being selected from the group consisting of an enzyme, a metal coordination complex, a co-factor, and an activator.

2. The sensing system as defined in claim 1, wherein the at least one pH altering moiety is the enzyme, and wherein the enzyme generates an acid or a base in a reaction with the secondary substrate.

3. The sensing system as defined in claim 2, wherein the enzyme is selected from the group consisting of hydrolases and oxidases.

4. The sensing system as defined in claim 1, wherein kinetics of the at least one pH altering moiety are at least 10 fold faster than kinetics of the polymerase.

5. The sensing system as defined in claim 1, wherein the at least one pH altering moiety is the enzyme, and wherein the complex further comprises a nucleic acid hairpin-enzyme inhibitor conjugate attached to the enzyme.

6. The sensing system as defined in claim 1, wherein:
    the at least one pH altering moiety is the enzyme; and
    the complex further includes a second enzyme attached to the polymerase.

7. The sensing system as defined in claim 1, wherein the complex is a fusion protein or a protein chimera.

8. The sensing system as defined in claim 1, wherein the conductive channel of the pH sensor is selected from the group consisting of a semi-conducting nanostructure, a graphene nanostructure, a metallic nanostructure, and a conducting polymer nanostructure.

9. The sensing system as defined in claim 1, further comprising:
    a support including a plurality of depressions separated by interstitial regions, wherein at least the conductive channel of the pH sensor is at a bottom of one of the plurality of depressions; and
    a plurality of additional pH sensors, wherein at least a conductive channel of each of the plurality of additional pH sensors is at a bottom of a respective one of the plurality of depressions.

10. The sensing system as defined in claim 9, wherein each of the plurality of depressions includes sidewalls, and wherein the sidewalls include a pH buffer material.

11. A kit, comprising:
a pH sensor, including:
two electrodes; and
a conductive channel operatively connected to the two electrodes; and
a fluid, including:
a liquid carrier; and
a complex in the liquid carrier, the complex including a polymerase linked to at least one enzyme that is to create a pH change within proximity of the conductive channel from consumption of a secondary substrate in a second fluid that is exposed to the pH sensor.

12. The kit as defined in claim 11, further comprising the second fluid, including:
a second liquid carrier; and
a labeled nucleotide, including:
a nucleotide;
a linking molecule attached to a terminal phosphate group of the nucleotide; and
a label attached to the linking molecule, the label being selected from the group consisting of a first group that enhances kinetics of the enzyme and a second group that slows kinetics of the enzyme.

13. The kit as defined in claim 12, wherein:
the secondary substrate is in the second fluid and is a separate molecule from the labeled nucleotide; and
the first group or the second group is to alter kinetics of an acid or base generating reaction involving the enzyme and the secondary substrate.

14. The kit as defined in claim 12, wherein:
the secondary substrate is in the second fluid and is a separate molecule from the labeled nucleotide;
the label is the second group that slows kinetics of the enzyme; and
the second group is selected from the group consisting of an allosteric inhibitor, a steric exclusion group, and a buffering group.

15. The kit as defined in claim 12, wherein:
the secondary substrate is in the second fluid and is a separate molecule from the labeled nucleotide;
the label is the first group that that enhances kinetics of the enzyme; and
the first group is a co-factor of the enzyme.

16. The kit as defined in claim 11, further comprising the second fluid, including:
a second liquid carrier; and
a labeled nucleotide, including:
a nucleotide; and
the secondary substrate attached to a base or a sugar of the nucleotide, wherein kinetics of the secondary substrate are at least 10 fold faster than kinetics of the polymerase.

17. A method, comprising:
introducing a fluid to a sensor array including a plurality of individually addressable conductive channels, thereby attaching a complex to at least some of the plurality of individually addressable conductive channels, the complex including:
a polymerase; and
a pH altering moiety linked to the polymerase, the pH altering moiety being selected from the group consisting of an enzyme that is to catalyze consumption of a secondary substrate in a solution that is to be exposed to the sensor array, a metal coordination complex that is to catalyze consumption of the secondary substrate in the solution that is to be exposed to the sensor array, and a co-factor or an activator of a catalyst label attached to a labeled nucleotide that is to be introduced to the sensor array.

18. A method, comprising:
selecting a pH altering moiety from the group consisting of an enzyme that is to catalyze consumption of a secondary substrate in a solution, a metal coordination complex that is to catalyze consumption of the secondary substrate in the solution, and a co-factor or an activator of a catalyst label attached to a labeled nucleotide;
conjugating a polymerase to the pH altering moiety to generate a complex; and
attaching the complex to a conductive channel operatively connected to two electrodes.

* * * * *